US007101978B2

(12) United States Patent
Watkins et al.

(10) Patent No.: US 7,101,978 B2

(45) Date of Patent: Sep. 5, 2006

(54) TNF-α BINDING MOLECULES

(75) Inventors: Jeffry D. Watkins, Encinitas, CA (US); Alain P. Vasserot, Carlsbad, CA (US); David Marquis, Encinitas, CA (US); William D. Huse, Del Mar, CA (US)

(73) Assignee: Applied Molecular Evolution, San Diego, CA (US)

( * ) Notice: Subject to any disclaimer, the term of this patent is extended or adjusted under 35 U.S.C. 154(b) by 705 days.

(21) Appl. No.: 10/338,552

(22) Filed: Jan. 8, 2003

(65) Prior Publication Data

US 2004/0131612 A1 Jul. 8, 2004

(51) Int. Cl.
*C07K 16/00* (2006.01)
*C07K 16/24* (2006.01)

(52) U.S. Cl. .............................. 530/387.9; 530/387.3; 530/388.23; 424/130.1; 424/133.1; 424/135.1; 424/158.1

(58) Field of Classification Search .................... None
See application file for complete search history.

(56) References Cited

U.S. PATENT DOCUMENTS 4,603,106 A 7/1986 Cerami et al.
4,677,063 A 6/1987 Mark et al.
4,677,064 A 6/1987 Mark et al.
4,822,776 A 4/1989 Cerami et al.
4,870,163 A 9/1989 Rubin et al.
4,879,226 A 11/1989 Wallace et al.
5,075,236 A 12/1991 Yone et al.
5,118,500 A 6/1992 Hänel et al.
5,145,676 A 9/1992 Fahey, III et al.
5,183,657 A 2/1993 Buurman
5,223,395 A 6/1993 Gero
5,231,024 A 7/1993 Moeller et al.
5,288,852 A 2/1994 Yamada et al.
5,360,716 A 11/1994 Ohmoto et al.
5,436,154 A 7/1995 Barbanti et al.
5,610,279 A 3/1997 Brockhaus et al.
5,616,321 A 4/1997 Hector et al.
5,616,688 A 4/1997 Cerami et al.
5,644,034 A 7/1997 Rathjen et al.
5,650,147 A 7/1997 Wolpe et al.
5,654,407 A 8/1997 Boyle et al.
5,656,272 A * 8/1997 Le et al. .................. 424/133.1
5,658,570 A 8/1997 Newman et al.
5,672,347 A 9/1997 Aggarwal et al.
5,686,428 A 11/1997 Eriksson et al.
5,698,195 A 12/1997 Le et al.
5,698,419 A 12/1997 Wolpe et al.
5,700,466 A 12/1997 Wolpe et al.
5,703,206 A 12/1997 Wolpe et al.
5,730,975 A 3/1998 Hotamisligil et al.
5,741,484 A 4/1998 Cerami et al.
5,741,488 A 4/1998 Feldman et al.
5,750,105 A 5/1998 Newman et al.
5,760,186 A 6/1998 Cerami et al.
5,795,967 A 8/1998 Aggarwal et al.
5,808,029 A 9/1998 Brockhaus et al.
5,817,763 A 10/1998 Cerami et al.
5,849,873 A 12/1998 Cerami et al.
5,859,205 A 1/1999 Adair et al.
5,863,535 A 1/1999 Cerami et al.
5,919,452 A 7/1999 Le et al.
5,942,222 A 8/1999 Wolpe et al.
5,958,413 A 9/1999 Anagnostopulos et al.
5,959,087 A 9/1999 Rathjen et al.
5,989,836 A 11/1999 Cerami et al.
5,994,510 A 11/1999 Adair et al.
6,015,557 A 1/2000 Tobinick et al.
6,015,558 A 1/2000 Hotamisligil et al.
6,019,969 A 2/2000 Cerami et al.
6,046,309 A 4/2000 Cerami et al.
6,090,382 A 7/2000 Salfeld et al.
6,114,517 A 9/2000 Monia et al.
6,177,077 B1 1/2001 Tobinick et al.
6,235,281 B1 5/2001 Stenzel et al.
6,258,562 B1 7/2001 Salfeld et al.
6,270,766 B1 8/2001 Feldman et al.
6,277,969 B1 8/2001 Le et al.
6,284,471 B1 9/2001 Le et al.
6,309,640 B1 10/2001 Cerami et al.
6,379,666 B1 4/2002 Tobinick (Continued)

FOREIGN PATENT DOCUMENTS

WO WO 95/03827 2/1995

(Continued)

OTHER PUBLICATIONS

Boyle, P, et al., "I. A Novel Monoclonal Human IgM Autoantibody which Binds Recombinant Human and Mouse Tumor Necrosis Factor-α", Cellular Immunology, 1993, pp. 556-568, vol. 152.

(Continued)

*Primary Examiner*—Lorraine Spector
*Assistant Examiner*—Shulamith H Shafer
(74) *Attorney, Agent, or Firm*—Alejandro Martinez; MaryAnn Wiskerchen

(57) ABSTRACT

The present invention relates to TNF-α binding molecules and nucleic acid sequences encoding TNF-α binding molecules. In particular, the present invention relates to TNF-α binding molecules with a high binding affinity, a high association rate, a low dissociation rate with regard to human TNF-α and that are capable of neutralizing TNF-α at low concentrations. Preferably, the TNF-α binding molecules of the present invention comprise light and/or heavy chain variable regions with fully human frameworks (e.g. human germline frameworks).

5 Claims, 14 Drawing Sheets

U.S. PATENT DOCUMENTS

| | | | | |
|---|---|---|---|---|
| 6,416,757 | B1 | 7/2002 | Rathjen et al. | |
| 6,419,927 | B1 | 7/2002 | Cerami et al. | |
| 6,419,934 | B1 | 7/2002 | Tobinick | |
| 6,419,944 | B1 | 7/2002 | Tobinick | |
| 6,423,321 | B1 | 7/2002 | Tobinick | |
| 6,428,787 | B1 | 8/2002 | Tobinick | |
| 6,448,380 | B1 | 9/2002 | Rathjen et al. | |
| 6,451,983 | B1 * | 9/2002 | Rathjen et al. | 530/388.23 |
| 6,498,237 | B1 | 12/2002 | Rathjen et al. | |
| 6,509,015 | B1 | 1/2003 | Salfeld et al. | |
| 6,537,549 | B1 | 3/2003 | Tobinick | |
| 6,555,111 | B1 | 4/2003 | Wallach et al. | |
| 6,593,458 | B1 | 7/2003 | Rathjen et al. | |
| 6,790,444 | B1 | 9/2004 | Le et al. | |
| 6,835,823 | B1 | 12/2004 | Le et al. | |
| 2003/0204066 | A1 | 10/2003 | Jumming et al. | |
| 2004/0063913 | A1 * | 4/2004 | Gram et al. | 530/388.23 |

FOREIGN PATENT DOCUMENTS

| | | | |
|---|---|---|---|
| WO | WO 97/30088 | | 8/1997 |
| WO | WO 98/22137 | | 5/1998 |
| WO | WO 98/51344 | | 11/1998 |
| WO | WO 01/94585 | A1 | 12/2001 |
| WO | WO 02/12502 | A2 | 2/2002 |
| WO | WO 03/042247 | A2 | 5/2003 |
| WO | WO 03/083061 | A2 | 10/2003 |

OTHER PUBLICATIONS

Boyle, P, et al., "II. The B5 Monoclonal Autoantibody Binds to Cell Surface TNFα on Human Lymphoid Cells and Cell Lines and Appears to Recognize a Novel Epitope", Cellular Immunology, 1993, pp. 569-581, vol. 152.

Breedveld, FC, et al., "Monoclonal antibody therapy of inflammatory rheumatic diseases", British Medical Bulletin, 1995, pp. 493-502, vol. 51, No. 2.

Brennan, FM, et al., "TNFα-A Pivotal Role in Rheumatoid Arthritis?", British Journal of Rheumatology, 1992, pp. 293-298, vol. 31.

Brensing-Küppers, J,et al., "The human immunoglobulin κ locus on yeast artificial chromosomes (YACs)", Gene, 1997, pp. 173-181, vol. 191.

Bringhman, TS, et al., "Monoclonal Antibodies to Human Tumor Necrosis Factors Alpha and Beta: Application for Affinity Purification, Immunoassays, and as Structural Probes", Hybridoma, 1987, pp. 489-507, vol. 6, No. 5.

Cox, JPL, et al., "A directory of human germ-line $V_{\chi}$ segments reveals a strong bias in their usage", Eur. J. Immonol., 1994, pp. 827-836, vol. 24.

Dick, AD, et al., "Inhibition of tumor necrosis factor activity minimizes target organ damage in experimental autoimmune uveoretinitis despite quantitatively normal activated T cell traffic to the retina", Eur. J. Immonol., 1996, pp. 1018-1025, vol. 26.

Elliott, MJ, et al., "Randomised double-blind comparison of chimeric monoclonal antibody to tumour necrosis factor α (cA2) versus placebo in rheumatoid arthritis", The Lancet, 1994, pp. 1105-1110, vol. 344.

Elliott, MJ, et al., "Repeated therapy with monoclonal antibody to tumour necrosis factor α (cA2) in patients with rheumatoid arthritis", Lancet, 1994, pp. 1125-1127, vol. 344.

Elliott, MJ, et al., "Treatment of Rheumatoid Arthritis with Chimeric Monoclonal Antibodies to Tumor Necrosis Factor α", Arthritis and Rheumatism, 1993, pp. 1681-1690, vol. 36, No. 12.

Exley, AR, et al., "Monoclonal antibody to TNF in severe septic shock", Lancet, 1990, pp. 1275-1277, vol. 335.

Feldman, M, et al., "Anti-Tumor Necrosis Factor-α Therapy of Rheumatoid Arthritis", Advances in Immunology, 1997, pp. 283-350, vol. 64.

Fendly, BM, et al., "Murine Monoclonal Antibodies Defining Neutralizing Epitopes on Tumor Necrosis Factor", Hybridoma, 1987, pp. 359-369, vol. 6, No. 4.

Fomsgaard, A., et al., "Auto-Antibodies to Tumour Necrosis Factor α in Healthy Humans and Patients with Inflammatory Diseases and Gram-Negative Bacterial Infections", Scand. J. Immunol., 1989, pp. 219-223, vol. 30.

Griffiths, AD, et al., "Human anti-self antibodies with high specificity from phage display libraries", The EMBO Journal, 1993, pp. 725-734, vol. 12, No. 2.

Hammerle, AF, et al., "Serum Proteins and Cytokines for Prediction of Sepsis?", Second Vienna Shock Forum, 1989, pp. 715-718.

Herve, P, et al., "Phase I-II Trial of a Monoclonal Anti-Tumor Necrosis Factor α Antibody for the Treatment of Refractory Severe Acute Graft-Versus-Host Disease", Blood, 1992, pp. 3362-3368, vol. 79, No. 12.

Hinshaw, LB, et al., "Survival of Primates in $LD_{100}$ Septic Shock Following Therapy With Antibody to Tumor Necrosis Factor (TNFα)", Circulatory Shock, 1990, pp. 279-292, vol. 30.

Johnson, G, et al., "Kabat Database and its applications: 30 years after the first variability plot", Nucleic Acid Research, 2001, pp. 214-218, vol. 28, No. 1.

Jones, EY, et al., "Structure of tumor necrosis factor", Nature, 1989, pp. 225-228, vol. 338.

Joop, MH, et al., "The Role of Tumor Necrosis Factor/Cachectin in Septic Shock," Second Vienna Shock Forum, 1989, pp. 463-466.

Kawasaki, K, et al., "Evolutionary dynamics of the human immunoglobulin κ locus and the germline repertoire of the Vκ genes", Eur. J. Immunol., 2001, pp. 1017-1028, vol. 31.

Kawasaki, K, et al., "One-Megabase Sequence Analysis of the Human Immunoglobulin λ Gene Locus", Genome Research, 1997, pp. 250-261, vol. 7.

Kempeni, J, "Preliminary results of early clinical trials with the fully human anti-TNFα monoclonal antibody D2E7", Ann. Rheum. Dis., 1999, pp. 170-172, vol. 58, (Suppl. I).

Knight, DM, et al., "Stable expression of cloned human antibody genes in murine myeloma cells", Hum. Antibod. Hybridoma, 1992, pp. 129-136, vol. 3.

Knight, DM, et al., "Construction and Initial Characterization of a Mouse-Human Chimeric Anti-TNF Antibody", Molecular Immunology, 1993, pp. 1443-1453, vol. 30, No. 16.

Liang, C-M et al., "Production and Characterization of Monoclonal Antibodies Against Recombinant Human Tumor Necrosis Factor/Cachectin", Biochemical and Biophysical Research Communications, 1986, pp. 847-854, vol. 137, No. 2.

Mathison, JC, et al., "Participation of Tumor Necrosis Factor in the Mediation of Gram Negative Bacterial Lipopolysaccharide-induced Injury in Rabbits", J. Clin. Invest., 1988, pp. 1925-1937, vol. 81.

Meager, A, et al., "Preparation and Characterization of Monoclonal Antibodies Directed Against Antigenic Determinants of Recombinant Human Tumour Necrosis Factor (rTNF)", Hybridoma, 1987, pp. 305-311, vol. 6, No. 3.

Michie, HR, et al., "Tumour necrosis factor and bacterial sepsis", Br. J. Surg., 1989, pp. 670-671, vol. 76.

Möller, A, et al., "Monoclonal Antibodies to Human Tumor Necrosis Factor α: In Vitro and In Vivo Application", Cytokine, 1990, pp. 162-169, vol. 2, No. 3.

Nakada, M, et al., "Neutralization of TNF by the Antibody cA2 Reveals Differential Regulation of Adhesion Molecule Expression on TNF-Activated Endothelial Cells", Cell Adhesion and Communication, 1998, pp. 491-503, vol. 5, No. 6.

Opal, SM, et al., "Efficacy of a Monoclonal Antibody Directed against Tumor Necrosis Factor in Protecting Neutropenic Rats from Lethal Infection with *Pseudomonas aeruginosa*", Journal of Infectious Diseases, 1990, pp. 1148-1152, vol. 161.

Scallon, BJ, et al., "Chimeric Anti-TNF-α Monoclonal Antibody cA2 Binds Recombinant Transmembrane TNF-α and Activates Immune Effector Functions", Cytokine, 1995, pp. 251-259, vol. 7, No. 3.

Schäble, et al., "The Variable Genes of the Human Immunoglobulin χ Locus", Biol. Chem. Hoppe-Seyler, 1993, pp. 1001-1022, vol. 374.

Siegel, SA, et al., "The Mouse/Human Chimeric Monoclonal Antibody cA2 Neutrailizes TNF in Vitro and Protects Transgenic Mice from Cachexia and TNF Lethality In Vivo", Cytokine, 1995, pp. 15-25, vol. 7, No. 1.

Shimamoto, Y, et al., "Monoclonal antibodies against human recombinant tumor necrosis factor: prevention of endotoxic shock", Immunol. Letters, 1988, pp. 311-317, vol. 17.
Silva, AT, et al., "Prophylactic and Therapeutic Effects of a Monoclonal Antibody to Tumor Necrosis Factor-α in Experimental Gram-Negative Shock", JID, 1990, pp. 421-427, vol. 162.
Simpson, SQ, et al., "Role of Tumor Necrosis Factor in Sepsis and Acute Lung Injury", Child Care Clinics, 1989, pp. 27-47, vol. 5, No. 1.
Smith, RA, et al., "The Active Form of Tumor Necrosis Factor Is a Trimer", Journal of Biological Chemistry, 1987, pp. 6951-6954, vol. 262, No. 15.
Tomlinson, IM, et al., "The structural repertoire of the human Vκ domain", EMBO Journal, 1995, pp. 4628-4638, vol. 14, No. 18.
Tomlinson, IM, et al., "The Repertoire of Human Germline VH Sequences Reveals about Fifty Groups of VH Segments with Different Hypervariable Loops", J. Mol. Biol., 1992, pp. 776-798, vol. 227.
Tracey, KJ, et al., "Anti-cachectin/TNF monoclonal antibodies prevent septic shock during lethal bacteraemia", Nature, 1987, pp. 662-664, vol. 330.
Vincent, J-L, et al., "Administration of Anti-TNF Antibody Improves Left Ventricular Function in Septic Shock Patients* Results of a Pilot Study", Chest, 1992, pp. 810-815, vol. 101, No. 3.
Waage, A, et al., "Association between tumour necrosis factor in serum and fatal outcome in patients with meningococcal disease", Lancet, 1987, pp. 355-357.
Watkins, PE, et al., "Treatment of ulcerative colitis in the cottontop tamarin using antibody to tumour necrosis factor alpha", Gut, 1997, pp. 628-633, vol. 40.
Williams, RO, et al., "Anti-tumor necrosis factor ameliorates joint disease in murine collagen-induced arthritis", Proc. Natl. Acad. Sci., 1992, pp. 9784-9788, vol. 89.
Wilson, PC, et al., "The Super-Information Age of Immunoglobulin Genetics", J. Exp. Med., 1998, pp. 1973-1975, vol. 188, No. 11.
Wu, TT, et al., "An Analysis of the Sequences of the Variable Regions of Bence Jones Proteins and Myeloma Light Chains and Their Implications for Anti-Body Complementarity", J. Exp. Med., 1970, pp. 211-250, vol. 132.

* cited by examiner

SEQ ID NO:1 - Hu1 light chain variable region amino acid sequence

EIVLTQSPDFQSVTPKEKVTITCRASQFVGSSIHWYQQKPDQSPKLLIKYASESMS
GVPSRFSGSGSGTDFTLTINSLEAEDAATYYCQQSHSWHFTFGQGTKVEIK

B.

SEQ ID NO:2 - Hu1 light chain variable region nucleic acid sequence

GAAATTGTGCTGACTCAGTCTCCAGACTTTCAGTCTGTGACTCCAAAAGAGA
AAGTCACCATCACCTGCAGGGCCAGTCAGTTCGTTGGCTCAAGCATCCACTG
GTACCAGCAGAAGCCAGATCAGTCTCCAAAGCTCCTCATCAAGTATGCTTCT
GAGTCTATGTCTGGGGTCCCCTCGAGGTTCAGTGGCAGTGGATCTGGGACAG
ATTTCACCCTCACCATCAATAGCCTGGAAGCTGAAGATGCTGCCACGTATTAC
TGTCAACAAAGTCATAGCTGGCATTTCACGTTCGGCCAAGGGACCAAGGTGG
AAATCAAA

SEQ ID NO:3 - Hu1 heavy chain variable region amino acid sequence

EVQLVESGGGLVQPGGSLRLSCAASGFTFSNHWMNWVRQAPGKGLEWVGEIRS
KSINSATHYAESVKGRFTISRDDSKNSLYLQMNSLKTEDTAVYYCARNYYGSTY
DHWGQGTLVTVSS

B.

SEQ ID NO:4 - Hu1 heavy chain variable region nucleic acid sequence

GAGGTGCAGCTGGTGGAGTCTGGGGGAGGCTTGGTCCAGCCTGGAGGGTCCC
TGAGACTCTCCTGTGCAGCCTCTGGATTCACTTTCAGTAACCACTGGATGAAC
TGGGTCCGCCAGGCTCCAGGGAAGGGGCTGGAGTGGGTTGGCGAAATTAGAT
CAAAATCTATTAATTCTGCAACACATTATGCGGAGTCTGTGAAAGGGAGATT
CACCATCTCAAGAGATGATTCAAAGAACTCACTGTACCTGCAGATGAACAGC
CTGAAAACCGAGGACACGGCCGTGTATTACTGTGCTAGAAATTACTACGGTA
GTACCTACGACCATTGGGGCCAAGGGACCCTGGTCACCGTCTCCTCA

SEQ ID NO:5 - A10K light chain variable region amino acid sequence

EIVLTQSPDFQSVTPKEKVTITCRASQFVGYSIHWYQQKPDQSPKLLIKYASESRS
GVPSRFSGSGSGTDFTLTINSLEAEDAATYYCQQSHSWHFTFGQGTKVEIK

B.

SEQ ID NO:6 - A10K light chain variable region nucleic acid sequence

GAAATTGTGCTGACTCAGTCTCCAGACTTTCAGTCTGTGACTCCAAAAGAGA
AAGTCACCATCACCTGCAGGGCCAGTCAGTTCGTTGGCTATAGCATCCACTG
GTACCAGCAGAAGCCAGATCAGTCTCCAAAGCTCCTCATCAAGTATGCTTCT
GAGTCTAGGTCTGGGGTCCCCTCGAGGTTCAGTGGCAGTGGATCTGGGACAG
ATTTCACCCTCACCATCAATAGCCTGGAAGCTGAAGATGCTGCCACGTATTAC
TGTCAACAAAGTCATAGCTGGCATTTCACGTTCGGCCAAGGGACCAAGGTGG
AAATCAAA

SEQ ID NO:7 - A10K heavy chain amino acid sequence

EVQLVESGGGLVQPGGSLRLSCAASGFKFSNHWMNWVRQAPGKGLEWVGEIRS
KSMNSATHYAESVKGRFTISRDDSKNSLYLQMNSLKTEDTAVYYCARNYYGST
YDHWGQGTLVTVSS

B.

SEQ ID NO:8 - A10K heavy chain nucleic acid sequence

GAGGTGCAGCTGGTGGAGTCTGGGGGAGGCTTGGTCCAGCCTGGAGGGTCCC
TGAGACTCTCCTGTGCAGCCTCTGGATTCCCTTTCAGTAACCACTGGATGAAC
TGGGTCCGCCAGGCTCCAGGGAAGGGGCTGGAGTGGGTTGGCGAAATTAGAT
CAAAATCTATGAATTCTGCAACACATTATGCGGAGTCTGTGAAAGGGAGATT
CACCATCTCAAGAGATGATTCAAAGAACTCACTGTACCTGCAGATGAACAGC
CTGAAAACCGAGGACACGGCCGTGTATTACTGTGCTAGAAATTACTACGGTA
GTACCTACGACCATTGGGGCCAAGGGACCCTGGTCACCGTCTCCTCA

FIGURE 5

A. Amino acid sequence of a human light chain framework region with interspersed CDR sequences labeled

(FRL1 - SEQ ID NO:57) (CDRL1) (FRL2 - SEQ ID NO:58) (CDRL2)
EIVLTQSPDFQSVTPKEKVTITCXXXXXXXXXXXWYQQKPDQSPKLLIKXXXXXXX (FRL3 - SEQ ID NO:59) (CDRL3) (FRL4 - SEQ ID NO:60)
GVPSRFSGSGSGTDFTLTINSLEAEDAATYYCXXXXXXXXXFGQGTKVEIK

B. Nucleic acid sequence of a human light chain framework region with interspersed CDR sequences labeled

(FRL1 - SEQ ID NO:61)
GAAATTGTGCTGACTCAGTCTCCAGACTTTCAGTCTGTGACTCCAAAAGAGAAAG (CDRL1)
TCACCATCACCTGCXXXXXXXXXXXXXXXXXXXXXXXXXXXXXXXXXTGGTAC (FRL2 - SEQ ID NO:62) (CDRL2)
CAGCAGAAGCCAGATCAGTCTCCAAAGCTCCTCATCAAGXXXXXXXXXXXXXX (CDRL2 cont.) (FRL3 - SEQ ID NO:63)
XXXXXXXGGGGTCCCCTCGAGGTTCAGTGGCAGTGGATCTGGGACAGATTTCAC

CCTCACCATCAATAGCCTGGAAGCTGAAGATGCTGCCACGTATTACTGT (CDRL3) (FRL4 - SEQ ID NO:64)
XXXXXXXXXXXXXXXXXXXXXXXXXXXTTCGGCCAAGGGACCAAGGTGGAAA

TCAAA

FIGURE 6

A. Amino acid sequence of a human heavy chain framework region with interspersed CDR sequences labeled

(FRH1 - SEQ ID NO:65) (CDRH1) (FRH2 - SEQ ID NO:66)
EVQLVESGGGLVQPGGSLRLSCAASXXXXXXXXXXWVRQAPGKGLEWVG (CDRH2) (FRH3 - SEQ ID NO:67)
XXXXXXXXXXXXXXXXXXXRFTISRDDSKNSLYLQMNSLKTEDTAVYYCAR (CDRH3) (FRH4 - SEQ ID NO:68)
XXXXXXXXXWGQGTLVTVSS

B. Nucleic acid sequence of a human heavy chain framework region with interspersed CDR sequences labeled

(FRH1 - SEQ ID NO:69)
GAGGTGCAGCTGGTGGAGTCTGGGGGAGGCTTGGTCCAGCCTGGAGGGTCCCTG (CDRH1)
AGACTCTCCTGTGCAGCCTCTXXXXXXXXXXXXXXXXXXXXXXXXXXXXXXTG (FRH2 - SEQ ID NO:70) (CDRH2)
GGTCCGCCAGGCTCCAGGGAAGGGGCTGGAGTGGGTTGGCXXXXXXXXXXXXX (CDRH2 cont.)
XXXXXXXXXXXXXXXXXXXXXXXXXXXXXXXXXXXXXXXXXXXXAGATTCAC (FRH3 - SEQ ID NO:71)
CATCTCAAGAGATGATTCAAAGAACTCACTGTACCTGCAGATGAACAGCCTGAA (CDRH3)
AACCGAGGACACGGCCGTGTATTACTGTGCTAGAXXXXXXXXXXXXXXXXXXX (CDRH3) (FRH4 - SEQ ID NO:72)
XXXXXXXXTGGGGCCAAGGGACCCTGGTCACCGTCTCCTCA Elisa Assay L929 Assay L929 Assay L929 Assay Polyarthritis Model

FIGURE 14

A. SEQ ID NO:85 - Human CL Sequence

TCAGCCTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCACA
CCTTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAATC
ACAAGCCCAGCAACACCAAGGTGGACAAGAAAGCAGAGCCCAAATCTTCT
ACTAGTGTTCTC*TACCCATATGATGTACCTGATTATGCATCA*TAG

Note: This CH1 sequence contains the first six IgG1 hinge region residues (in bold) and fused to a HA decapeptide tag (italic) through a four amino acid linker (underlined).

B. SEQ ID NO:86 - Human CH1 Sequence

CGAACTGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAG
AGGCCAAAGTACAGTGGAAGGTGGATAACGCCCTCCAATCGGGTAACTCCCA
GGAGAGTGTCACAGAGCAGGACAGCAAGGACAGCACCTACAGCCTCAGCAG
CACCCTGACGCTGAGCAAAGCAGACTACGAGAAACACAAAGTCTACGCCTGC
GAAGTCACCCATCAGGGCCTGAGCTCGCCCGTCACAAAGAGCTTCAACAGGG
GAGAGTCTTAG

TNF-α BINDING MOLECULES

FIELD OF THE INVENTION

The present invention relates to TNF-α binding molecules and nucleic acid sequences encoding TNF-α binding molecules. In particular, the present invention relates to TNF-α binding molecules with a high binding affinity, a high association rate, a low dissociation rate with regard to human TNF-α, and that are capable of preventing TNF-α mediated cytotoxicity at low concentrations. Preferably, the TNF-α binding molecules of the present invention comprise light and/or heavy chain variable regions with fully human frameworks (e.g. human germline frameworks).

BACKGROUND OF THE INVENTION

Tumor necrosis factor alpha (TNF-α) is a cytokine produced by numerous cell types, including monocytes and macrophages, that was originally identified based on its ability to induce the necrosis of certain mouse tumors. Subsequently, a factor termed cachectin, associated with cachexia, was shown to be identical to TNF-α. TNF-α has been implicated in the pathophysiology of a variety of other human diseases and disorders, including shock, sepsis, infections, autoimmune diseases, transplant rejection and graft-versus-host disease.

Because of the harmful role of human TNF-α (hTNF-α) in a variety of human disorders, therapeutic strategies have been designed to inhibit or counteract hTNF-α activity. In particular, antibodies that bind to, and neutralize, hTNF-α have been sought as a means to inhibit hTNF-α activity. Some of the earliest of such antibodies were mouse monoclonal antibodies (mAbs), secreted by hybridomas prepared from lymphocytes of mice immunized with hTNF-α (see e.g., U.S. Pat. No. 5,231,024 to Moeller et al.). While these mouse anti-hTNF-α antibodies often displayed high affinity for hTNF-α and were able to neutralize hTNF-α activity, their use in vivo has been limited by problems associated with the administration of mouse antibodies to humans, such as a short serum half-life, an inability to trigger certain human effector functions, and elicitation of an unwanted immune response against the mouse antibody in a human (the "human anti-mouse antibody" (HAMA) reaction).

In an attempt to overcome the problems associated with the use of fully murine antibodies in humans, murine anti-hTNF-α antibodies have been genetically engineered to be more "human-like." For example, chimeric antibodies, in which the variable regions of the antibody chains are murine-derived and the constant regions of the antibody chains are human-derived, have been prepared (e.g., U.S. Pat. No. 5,698,195, herein incorporated by reference). Additionally, humanized antibodies, in which the hypervariable domains and a number of the framework residues of the antibody variable regions are murine-derived but the remainder of the variable regions and the antibody constant regions are human-derived, have also been prepared (e.g. U.S. Pat. No. 5,994,510 to Adair et al., herein incorporated by reference). However, because these antibodies still retain a substantial number of murine residues, they still may elicit an unwanted immune reaction, the human anti-chimeric antibody (HACA) reaction, especially when administered for prolonged periods (see e.g., Elliott, et al., (1994) Lancet 344:1125–1127; and Elliot, et al., (1994) Lancet 344:1105–1110).

Attempts have been made to further limit or eliminate the presence of murine sequences in anti-TNF-α antibodies. For example, human monoclonal autoantibodies against hTNF-α have been prepared using human hybridoma techniques (e.g., U.S. Pat. No. 5,654,407 to Boyle, herein incorporated by reference). However, these hybridoma-derived monoclonal autoantibodies were reported to have an affinity for hTNF-α that was too low to measure by conventional methods, were unable to bind soluble hTNF-α and were unable to neutralize hTNF-α-induced cytotoxicity (see Boyle, et al., (1993) Cell. Immunol. 152:556–581). Moreover, the success of the human hybridoma technique generally depends upon the natural presence in human peripheral blood of lymphocytes producing autoantibodies specific for hTNF-α.

An alternative to naturally-occurring human anti-hTNF-α antibodies would be a recombinant hTNF-α antibody. Recombinant human antibodies that bind hTNF-α with relatively low affinity (i.e., $K_d$ of about $10^{-7}$ M) and a relatively fast dissociation rate (i.e., $k_{off}$ of about $10^{-2}$ $s^{-1}$) have been described (Griffiths, A. D., et al. (1993) EMBO J. 12:725–734). However, because of their relatively fast dissociation kinetics, and relatively low affinity, these antibodies may not be suitable for therapeutic use. Additionally, recombinant human anti-hTNF-α antibodies with moderate binding affinities ($K_d$ of about $6\times10^{-10}$ M), dissociation rates ($k_{off}$ of about $8.8\times10^{-5}$ $s^{-1}$), association rates ($k_{on}$ of about $1.9\times10^{5}$ $M^{-1}s^{-1}$), and neutralization potential ($IC_{50}$ of about $1.25\times10^{-10}$) have been described (See, D2E7 antibody in U.S. Pat. No. 6,258,562, herein incorporated by reference).

Accordingly, what is needed, are TNF-α binding molecules with a high binding affinity, a high association rate, a low dissociation rate and improved neutralization properties with regard to human TNF-α, as well as TNF-α binding molecules with significantly reduced immunogenicity in humans.

SUMMARY OF THE INVENTION

The present invention provides TNF-α binding molecules and nucleic acid sequences encoding TNF-α binding molecules. In particular, the present invention provides TNF-α binding molecules with a high binding affinity, a high association rate, a low dissociation rate with regard to human TNF-α, and enhanced neutralization properties in vitro and in vivo. Preferably, the TNF-α binding molecules of the present invention comprise light and/or heavy chain variable regions with fully human frameworks. In particularly preferred embodiments, the TNF-α binding molecules of the present invention comprise light and/or heavy chain variable regions with germline frameworks (e.g. human germline frameworks).

In some embodiments, the present invention provides compositions comprising a peptide, or a nucleic acid sequence encoding a peptide, wherein the peptide comprises an amino acid sequence selected from SEQ ID NOs: 11, 13, and 15. In other embodiments, the peptide further comprises one or more amino acid sequences selected from SEQ ID NOs: 19, 21, 23, 25, 27, 29, 31, 33, 35, 37, 39, 41, 43, 45, 47, 49, 51, 53, and 55.

In certain embodiments, the present invention provides compositions comprising a peptide, or a nucleic acid sequence encoding a peptide, wherein the peptide comprises an amino acid sequence selected from SEQ ID NOs: 21, 25, and 27. In other embodiments, the peptide further comprises one or more amino acid sequences selected from SEQ ID NOs: 9, 11, 13, 15, 17, 33, 35, 37, 39, 41, 43, 45, 47, 49, 51, 53 and 55.

In additional embodiments, the present invention provides compositions comprising a peptide, or a nucleic acid sequence encoding a peptide, wherein the peptide comprises an amino acid sequence shown in SEQ ID NO: 33. In certain embodiments, the peptide further comprises one or more amino acid sequences selected from SEQ ID NOs: 9, 11, 13, 15, 17, 19, 21, 23, 25, 27, 29, 31, 35, 37, 39, 41, 43, 45, 47, 49, 51, 53, and 55.

In some embodiments, the present invention provides compositions comprising a peptide, or a nucleic acid sequence encoding a peptide, wherein the peptide comprises an amino acid sequence selected from SEQ ID NOs: 35, 37, and 39. In other embodiments, the peptide further comprises one or more amino acid sequences selected from SEQ ID NOs: 9, 11, 13, 15, 17, 19, 21, 23, 25, 27, 29, 31, 33, 43, 45, 47, 49, 51, 53, and 55.

In particular embodiments, the present invention provides compositions comprising a peptide, or a nucleic acid sequence encoding a peptide, wherein the peptide comprises an amino acid sequence selected from SEQ ID NOs: 45 and 49. In other embodiments, the peptide further comprises one or more amino acid sequences selected from SEQ ID NOs: 9, 11, 13, 15, 17, 19, 21, 23, 25, 27, 29, 31, 33, 35, 37, 39, 41, and 53.

In certain embodiments, the present invention provides compositions comprising a peptide, or a nucleic acid sequence encoding a peptide, wherein the peptide comprises an amino acid shown in SEQ ID NO: 53. In additional embodiments, the peptide further comprises one or more amino acid sequences selected from SEQ ID NOs: 9, 11, 13, 15, 17, 19, 21, 23, 25, 27, 29, 31, 33, 35, 37, 39, 41, 43, 45, 47, 49, 51, and 55.

In some embodiments, the TNF-α binding molecule is a TNF-α binding peptide or polypeptide. In certain embodiments, the TNF-α binding peptide comprises an anti-TNF-α antibody or anti-TNF-α antibody fragment (e.g., Fab, $F(ab')_2$, etc). In other embodiments, the peptide comprises a light and/or heavy chain variable region. In particular embodiments, the light chain variable region and/or heavy chain variable region comprises a framework region. In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g. human germline). In other embodiments, at least FRH1, FRH2, FRH3, or FRH4 is a germline sequence (e.g. human germline). In preferred embodiments, the framework region is a fully human framework region (e.g. the human framework regions shown in FIGS. 5 and 6). In some embodiments, the framework region comprises SEQ ID NO: 57, 58, 59, 60 or combinations thereof. In other embodiments, the framework region comprises SEQ ID NO: 65, 66, 67, 68, or combinations thereof.

In some embodiments, the present invention provides compositions comprising an oligonucleotide, wherein the oligonucleotide comprises a nucleic acid sequence selected from SEQ ID NO: 12, 14, or 16. In other embodiments, the oligonucleotide further comprises one or more nucleic acid sequences selected from SEQ ID NOs: 20, 22, 24, 26, 28, 30, 32, 34, 36, 38, 40, 42, 44, 46, 48, 50, 52, 54, and 56.

In certain embodiments, the present invention provides compositions comprising an oligonucleotide, wherein the oligonucleotide comprises a nucleic acid sequence selected from SEQ ID NOs: 22, 26, and 28. In further embodiments, the oligonucleotide further comprises one or more nucleic acid sequences selected from SEQ ID NOs: 10, 12, 14, 16, 18, 34, 36, 38, 40, 42, 44, 46, 48, 50, 52, and 54.

In other embodiments, the present invention provides compositions comprising an oligonucleotide, wherein the oligonucleotide comprises a nucleic acid sequence shown in SEQ ID NO: 34. In certain embodiments, the oligonucleotide further comprises one or more nucleic acid sequences selected from SEQ ID NOs: 10, 12, 14, 16, 18, 20, 22, 24, 26, 28, 30, 32, 36, 38, 40, 42, 44, 46, 48, 50, 52 and 54.

In particular embodiments, the present invention provides compositions comprising an oligonucleotide, wherein the oligonucleotide comprises a nucleic acid sequence selected from SEQ ID NOs: 36, 38, and 40. In additional embodiments, the oligonucleotide further comprises one or more nucleic acid sequences selected from SEQ ID NOs: 10, 12, 14, 16, 18, 20, 22, 24, 26, 28, 30, 32, 34, 44, 46, 48, 50, 52, and 54.

In other embodiments, the present invention provides compositions comprising an oligonucleotide, wherein the oligonucleotide comprises a nucleic acid sequence selected from SEQ ID NOs: 46 and 50. In some embodiments, the oligonucleotide further comprises one or more nucleic acid sequences selected from SEQ ID NOs: 10, 12, 14, 16, 18, 20, 22, 24, 26, 28, 30, 32, 34, 36, 38, 40, 42, and 54.

In additional embodiments, the present invention provides compositions comprising an oligonucleotide, wherein the oligonucleotide comprises a nucleic acid sequence shown in SEQ ID NO: 54. In certain embodiments, the oligonucleotide further comprises one or more nucleic acid sequences selected from SEQ ID NOs: 10, 12, 14, 16, 18, 20, 22, 24, 26, 28, 30, 32, 34, 36, 38, 40, 42, 44, 46, 48, 50, and 52.

In some embodiments, the oligonucleotide further comprises a vector sequence. In other embodiments, the oligonucleotide further comprises a nucleic acid sequence encoding an antibody variable region framework. In preferred embodiments, the framework is fully human. In additional embodiments, the oligonucleotide further comprises a nucleic acid sequence encoding an antibody constant region. In some embodiments, the oligonucleotide comprises a framework region selected from SEQ ID NO: 61, 62, 63, 64, 69, 70, 71, 72, or combinations thereof.

In some embodiments, the present invention provides compositions comprising a TNF-α binding molecule, or an oligonucleotide encoding a TNF-α binding molecule, wherein the TNF-α binding molecule comprises: i) a CDRL3 sequence comprising SEQ ID NO: 33, and ii) a CDRH3 comprising SEQ ID NO: 53. In particular embodiments, the TNF-α molecule comprises the hu1 Fab (e.g., an IgG with the variable regions present in the hu1 Fab fragment).

In certain embodiments, the TNF-α binding molecule further comprises iii) a CDRL1 sequence comprising SEQ ID NO: 11, and iv) a CDRL2 sequence comprising SEQ ID NO:21. In other embodiments, the TNF-α binding molecule further comprises: v) a CDRH1 sequence comprising SEQ ID NO: 37, and vi) a CDRH2 sequence comprising SEQ ID NO: 49. In some embodiments, the TNF-α binding molecule comprises the 2C6K Fab (e.g., an IgG with the variable regions present in the 2C6K Fab fragment). In additional embodiments, the TNF-α binding molecule further comprises: v) a CDRH1 sequence comprising SEQ ID NO: 39, and vi) a CDRH2 sequence comprising SEQ ID NO: 49. In particular embodiments, the TNF-α binding molecule comprises the 2C6P Fab (e.g., an IgG with the variable regions present in the 2C6P Fab fragment).

In some embodiments, the TNF-α binding molecule further comprises: iii) a CDRL1 sequence comprising SEQ ID NO: 11, and iv) a CDRL2 sequence comprising SEQ ID NO: 25. In other embodiments, the TNF-α binding molecule further comprises: v) a CDRH1 sequence comprising SEQ ID NO: 37, and vi) a CDRH2 sequence comprising SEQ ID NO: 55. In particular embodiments, the TNF-α binding molecule comprises the 2E7K Fab (e.g., an IgG with the variable regions present in the 2E7K Fab fragment). In other embodiments, the TNF-α binding molecule further comprises: v) a CDRH1 sequence comprising SEQ ID NO: 39, and vi) a CDRH2 sequence comprising SEQ ID NO: 55. In particular embodiments, the TNF-α binding molecule comprises the 2E7P Fab (e.g., an IgG with the variable regions present in the 2E7P Fab fragment).

In additional embodiments, the TNF-α binding molecule further comprises: iii) a CDRL1 sequence comprising SEQ ID NO: 13, and iv) a CDRL2 sequence comprising SEQ ID NO: 27. In some embodiments, the TNF-α binding molecule further comprises: v) a CDRH1 sequence comprising SEQ ID NO: 37, and vi) a CDRH2 sequence comprising SEQ ID NO: 55. In particular embodiments, the TNF-α binding molecule comprises the A9K Fab (e.g., an IgG with the variable regions present in the A9K Fab fragment). In certain embodiments, the TNF-α binding molecule further comprises: v) a CDRH1 sequence comprising SEQ ID NO: 39, and vi) a CDRH2 sequence comprising SEQ ID NO: 55. In particular embodiments, the TNF-α binding molecule comprises the A9P Fab (e.g., an IgG with the variable regions present in the A9P Fab fragment).

In some embodiments, the TNF-α binding molecule further comprises: iii) a CDRL1 sequence comprising SEQ ID NO: 15, and iv) a CDRL2 sequence comprising SEQ ID NO: 25. In other embodiments, the TNF-α binding molecule further comprises: v) a CDRH1 sequence comprising SEQ ID NO: 37, and vi) a CDRH2 sequence comprising SEQ ID NO: 45. In particular embodiments, the TNF-α binding molecule comprises the A10K Fab (e.g., an IgG with the variable regions present in the A10K Fab fragment). In other embodiments, the TNF-α binding molecule further comprises: v) a CDRH1 sequence comprising SEQ ID NO: 39, and vi) a CDRH2 sequence comprising SEQ ID NO: 45. In particular embodiments, the TNF-α binding molecule comprises the A10P Fab (e.g., an IgG with the variable regions present in the A10P Fab fragment).

In some embodiments, the TNF-α binding molecule further comprises: iii) a CDRL1 sequence comprising SEQ ID NO: 9, and iv) a CDRL2 sequence comprising SEQ ID NO: 19. In other embodiments, the TNF-α binding molecule further comprises: v) a CDRH1 sequence comprising SEQ ID NO: 35, and vi) a CDRH2 sequence comprising SEQ ID NO:43.

In certain embodiments, the TNF-α binding molecule further comprises a light chain variable region, wherein the light chain variable region comprises a framework region. In some embodiments, the light chain variable region comprises light chain framework regions selected from SEQ ID NOs: 57, 58, 59, 60, and combinations thereof. In preferred embodiments, the framework region is a fully human framework. In particularly preferred embodiments, the framework region is a germline framework (e.g. human or other animal germline framework).

In some embodiments, the TNF-α binding molecule further comprises a heavy chain variable region, wherein the heavy chain variable region comprises a framework region. In certain embodiments, the heavy chain variable region comprises a heavy chain framework regions selected from SEQ ID NOs: 65, 66, 67, 68, and combinations thereof. In preferred embodiments, the framework is a fully human framework. In particularly preferred embodiments, the framework region is a germline framework (e.g. human or other animal germline framework).

In certain embodiments, the present invention provides compositions comprising a light chain variable region, or a nucleic acid sequence encoding a light chain variable region, wherein the light chain variable region comprises an amino acid sequence selected from SEQ ID NOs:1 and 5. In other embodiments, the present invention provides compositions comprising an oligonucleotide encoding a light chain variable region, wherein the oligonucleotide comprises SEQ ID NO: 2 or SEQ ID NO: 6.

In some embodiments, the present invention provides compositions comprising a heavy chain variable region, or a nucleic acid sequence encoding a heavy chain variable region, wherein the heavy chain variable region comprises an amino acid sequence selected from SEQ ID NOs: 3 and 7. In particular embodiments, the present invention provides compositions comprising an oligonucleotide encoding a heavy chain variable region, wherein the oligonucleotide comprises SEQ ID NO: 4 or SEQ ID NO: 8.

In some embodiments, the present invention provides a computer readable medium that encodes a representation of a nucleic acid or amino acid sequence selected from SEQ ID NOs: 1–84, or the complement thereof. In certain embodiments, the representation of these sequences, when delivered to a computer processor, may be displayed to a user (e.g., over the internet).

In some embodiments, the present invention provides the complement of the nucleic acid sequences described herein (see e.g. Tables 1–3). In some embodiments, the present invention provides sequences that hybridize under high, medium or low stringency with the nucleic acid sequences described herein (see e.g. Tables 1–3).

In certain embodiments, the present invention provides compositions comprising a TNF-α binding molecule that has an association rate constant ($k_{on}$) for human TNF-α of $3.0\times10^{6}$ $M^{-1}$ $s^{-1}$ or greater. In other embodiments, the association rate constant is $4.0\times10^{6}$ $M^{-1}$ $s^{-1}$ or greater (e.g., about $4.1\times10^{6}$ $M^{-1}$ $s^{-1}$, about $5.5\times10^{6}$ $M^{-1}$ $s^{-1}$, or about $7.0\times10^{6}$ $M^{-1}$). In other embodiments, the association rate constant is between about $3.0\times10^{6}$ $M^{-1}$ $s^{-1}$ and about $7.5\times10^{6}$ $M^{-1}$ $s^{-1}$ (e.g., between about $3.5\times10^{6}$ $M^{-1}$ $s^{-1}$ and about $7.0\times10^{6}$ $M^{-1}$ $s^{-1}$, or between about $4.0\times10^{6}$ $M^{-1}$ $s^{-1}$ and about $6.0\times10^{6}$ $M^{-1}$ $s^{-1}$).

In some embodiments, the association rate constant is determined by a kinetic exclusion assay (See, e.g., Chiu et al., (2001) Anal. Chem., 73:5477–5484; Blake, et al., (1996) Journal of Biological Chemistry, 271:27677–27685; Hongo, et al., (2000) Hybridoma, 19:303–315; Khosraviani, et al., (2000) Bioconjugate Chemistry, 11:267–277; and Powers, et al., (2001) Journal of Immunological Methods, 251:123–135, all of which are herein incorporated by reference). In particular embodiments, the kinetic exclusion assay is performed with a KinExA instrument (e.g., KinExA™3000 from Sapidyne Instruments, Boise, Id.), or similar device.

In further embodiments, the TNF-α binding molecule has a binding affinity ($K_d$) for human TNF-α of about $7.5\times10^{-12}$ M or less. In other embodiments, the binding affinity is about $5.0\times10^{-12}$ M or less. In certain embodiments, the binding affinity is about $3.0\times10^{-12}$ M or less. In some embodiments, the binding affinity is $2.2\times10^{-12}$ M or less. In yet other embodiments, the binding affinity is between about $7.2\times10^{-12}$ M and about $2.0\times10^{-12}$ M (e.g., between about $6.0\times10^{-12}$ M and about $3.0\times10^{-12}$ M, or between about $5.0\times10^{-12}$ M and about $4.0\times10^{-12}$ M). In particular embodiments, the binding affinity is determined by a kinetic exclusion assay (e.g., with a KinExA instrument).

In certain embodiments, the TNF-α binding molecule has a dissociation rate constant ($k_{off}$) for human TNF-α of about $1.0\times10^{-4}$ $s^{-1}$ or less. In some embodiments, the dissociation rate constant is about $1.0\times10^{-5}$ $s^{-1}$ or less, about $9.0\times10^{-6}$ $s^{-1}$ or less, or about $7.0\times^{-6}$ $s^{-1}$ or less. In other embodiments, the dissociation rate constant is between about $1.0\times10^{-4}$ $s^{-1}$ and about $8.0\times10^{-6}$ $s^{-1}$ (e.g., between about $1.0\times10^{-5}$ $s^{-1}$ and about $6.0\times10^{-6}$ $s^{-1}$). In certain embodiments, the dissociation rate is determined by a kinetic exclusion assay.

In some embodiments, the present invention provides compositions comprising a TNF-α binding molecule that neutralizes human TNF-α cytotoxicity in an in vitro, cell-based assay (see, e.g., Example 2) with an $EC_{50}$ of $1.0\times10^{-10}$ or less (e.g., $1.0\times10^{-10}$–$1.0\times10^{-11}$). In other embodiments, the TNF-α binding molecule neutralizes human TNF-α cytotoxicity in an in vitro, cell-based assay with an $EC_{50}$ of $7.0\times10^{-11}$ or less (e.g., $7.0\times10^{-11}$–$3.0\times10^{-11}$) In some embodiments, the TNF-α binding molecule neutralizes human TNF-α cytotoxicity in an in vitro, cell-based assay with an $EC_{50}$ of $2.0\times10^{-12}$ or less (e.g., $1.9\times10^{-12}$ or less, $1.8\times10^{-12}$ or less, $1.7\times10^{-12}$ or less, $1.6\times10^{-12}$ or less, $1.5\times10^{-12}$ or less, $1.3\times10^{-12}$ or less, $1.2\times10^{-12}$ or less, $1.1\times10^{-12}$ or less, $1.0\times10^{-12}$ or less, $0.8\times10^{-12}$ or less, etc.). In additional embodiments, the TNF-α binding molecule neutralizes human TNF-α cytotoxicity in an in vitro, cell-based assay with an $EC_{50}$ of $3.0\times10^{-12}$ or less (e.g., $3.0\times10^{-12}$–$2.0\times10^{-12}$). In particular embodiments, the neutralization assay is performed by treating L929 mouse fibroblasts with the molecules of the present invention and subsequently determining an effective concentration capable of preventing TNF-α mediated cell death.

In some embodiments, the TNF-α binding molecule comprises a light chain variable region and a heavy chain variable region. In certain embodiments, the light chain variable region comprises a fully human framework (see, e.g., FIG. 5). In some embodiments, the light chain variable region comprises a germline framework (e.g. human germline framework). In other embodiments, the heavy chain variable region comprises a fully human framework (see, e.g., FIG. 6). In additional embodiments, the heavy chain variable region comprises a germline framework (e.g. human germline framework). In particular embodiments, the TNF-α binding molecule comprises a Fab or $F(ab')_2$. In other embodiments, the TNF-α binding molecule comprises a Fab, and further comprises one or more constant regions (e.g., CH2 and/or CH3, see FIG. 13). In particular embodiments, the TNF-α binding molecule comprises an antibody (e.g., an antibody comprising a fully human framework with synthetic CDR sequences). In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

In some embodiments, amino acid modification(s) are introduced into the CH2 domain of an Fc region of a TNF-α binding molecule. Useful amino acid positions for modification in order to generate a variant IgG Fc region with altered Fc gamma receptor (FcγR) binding affinity or activity include any one or more of the following amino acid positions: 268, 269, 270, 272, 276, 278, 280, 283, 285, 286, 289, 290, 292, 293, 294, 295, 296, 298, 300 301, 303, 305, 307, 309, 331, 333, 334, 335, 337, 338, 340, 360, 373, 376, 416, 419, 430, 434, 435, 437, 438 or 439 of the Fc region of a TNF-α binding molecule. In preferred embodiments, the parent Fc region used as the template to generate such variants comprises a human IgG Fc region. In some embodiments, to generate an Fc region variant with reduced binding to the FcγR one may introduce an amino acid modification at any one or more of the following amino acid positions: 252, 254, 265, 268, 269, 270, 272, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439 of the Fc region of a TNF-α binding molecule. In particular embodiments, Fc region variants with improved binding to one or more FcγRs may also be made. Such Fc region variants may comprise an amino acid modification at any one or more of the following amino acid positions: 280, 283, 285, 286, 290, 294, 295, 298, 300, 301, 305, 307, 309, 312, 315, 331, 333, 334, 337, 340, 360, 378, 398 or 430 of the Fc region of a TNF-α binding molecule.

In certain embodiments, the present invention provides TNF-α binding molecules comprising a variant of a parent polypeptide having an Fc region, wherein the variant binds an FcγR with higher affinity than said parent polypeptide, and/or interacts with an FcγR with a higher assay signal, and/or mediates antibody-dependent cell-mediated cytotoxicity (ADCC) in the presence of effector cells, and comprises at least one amino acid modification at position 300 in the Fc region. In certain embodiments, the amino acid modification is Y3001. In other embodiments, the amino acid modification is Y300L.

In some embodiments, the present invention provides TNF-α binding molecules comprising a variant of a parent polypeptide having an Fc region, wherein the variant binds an Fc gamma receptor III (FcγRIII) with higher affinity, or the variant interacts with an FcγRIII with a higher assay signal, than the parent polypeptide, and/or mediates antibody-dependent cell-mediated cytotoxicity (ADCC) in the presence of effector cells, and comprises at least one amino acid modification at position 295 in the Fc region. In certain embodiments, the amino acid modification is Q295K or Q295L.

In particular embodiments, the present invention provides TNF-α binding molecules comprising a variant of a parent polypeptide having an Fc region, wherein the variant binds an FcγRII with higher affinity, or the variant interacts with an FcγRII with a higher assay signal, than the parent polypeptide, and/or mediates antibody-dependent cell-mediated cytotoxicity (ADCC) in the presence of effector cells, and comprises at least one amino acid modification at position 294 in the Fc region. In certain embodiments, the amino acid modification is E294N.

In other embodiments, the present invention provides TNF-α binding molecules comprising a variant of a parent polypeptide having an Fc region, wherein the variant has a binding affinity, or assay signal, for FcγRII or FcγRIIb that is approximately 0.25 or less as measured in an ELISA FcγR binding assay. In certain embodiments, the variant comprises at least one amino acid modification at position 296 in the Fc region. In particular embodiments, the amino acid modification at position 296 is Y296P. In other embodiments, the variant comprises at least one amino acid modification at position 298 in the Fc region. In some embodiments, the amino acid modification at position 298 is S298P.

In particular embodiments, the present invention provides TNF-α binding molecules comprising a variant of a parent polypeptide having an Fc region, wherein the variant binds an FcγRIII with greater affinity, and FcγRIIb with less affinity, than the parent polypeptide and the variant comprises a S298N amino acid modification in the Fc region. In some embodiments, the present invention provides compositions comprising a variant of a parent polypeptide having an Fc region, wherein the variant interacts with an FcγRII with a higher assay signal, and FcγRIIb with lower assay signal, than the parent polypeptide and the variant comprises a S298N amino acid modification in the Fc region.

In other embodiments, the present invention provides TNF-α binding molecules comprising a variant of a parent polypeptide having an Fc region, wherein the variant binds an FcγRII with greater affinity, and FcγRIIb with less affinity, than the parent polypeptide and the variant comprises a S298V amino acid modification in the Fc region. In some embodiments, the present invention provides compositions comprising a variant of a parent polypeptide having an Fc region, wherein the variant interacts with an FcγRII with a higher assay signal, and FcγRIIb with a lower assay signal, than the parent polypeptide and the variant comprises a S298V amino acid modification in the Fc region.

In some embodiments, the present invention provides TNF-α binding molecules comprising a variant of a parent polypeptide having an Fc region, wherein the variant binds an FcγRIII with greater affinity, and FcγRIIb with less affinity, than the parent polypeptide and the variant comprises a S298D amino acid modification in the Fc region. In other embodiments, the present invention provides compositions comprising a variant of a parent polypeptide having an Fc region, wherein the variant interacts with an FcγRIII with a higher assay signal, and FcγRIIb with a lower assay signal, than the parent polypeptide and the variant comprises a S298D amino acid modification in the Fc region.

In certain embodiments, the present invention provides TNF-α binding molecules comprising a variant of a parent polypeptide having an Fc region, wherein the variant has a binding affinity, or assay signal, for FcγRII or FcγRIIb that is approximately 0.25 or less as measured in an ELISA FcγR binding assay, and wherein the variant comprises at least one amino acid modification at position 298 of the Fc region. In particular embodiments, the amino acid modification at position 298 is S298P.

The polypeptide variants described above may be subjected to further modifications, depending on the desired or intended use of the polypeptide. Such modifications may involve, for example, further alteration of the amino acid sequence (substitution, insertion and/or deletion of amino acid residues), fusion to heterologous polypeptide(s) and/or covalent modifications. Such further modifications may be made prior to, simultaneously with, or following, the amino acid modification(s) disclosed above which result in an alteration of Fc receptor binding and/or ADCC activity.

Alternatively or additionally, it may be useful to combine amino acid modifications with one or more further amino acid modifications that alter C1q binding and/or the complement dependent cytotoxicity function of the Fc region of a TNF-α binding molecule. The starting polypeptide of particular interest may be one that binds to C1q and displays complement dependent cytotoxicity (CDC). Amino acid substitutions described herein may serve to alter the ability of the starting polypeptide to bind to C1q and/or modify its complement dependent cytotoxicity function (e.g., to reduce and preferably abolish these effector functions). However, polypeptides comprising substitutions at one or more of the described positions with improved C1q binding and/or complement dependent cytotoxicity (CDC) function are contemplated herein. For example, the starting polypeptide may be unable to bind C1q and/or mediate CDC and may be modified according to the teachings herein such that it acquires these further effector functions. Moreover, polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of a TNF-α binding molecule with altered effector function, e.g., by modifying C1q binding and/or FcγR binding and thereby changing CDC activity and/or ADCC activity. For example, one can generate a variant Fc region of a TNF-α binding molecule with improved C1q binding and improved FcγRIIbinding (e.g., having both improved ADCC activity and improved CDC activity). Alternatively, where one desires that effector function be reduced or ablated, one may engineer a variant Fc region with reduced CDC activity and/or reduced ADCC activity. In other embodiments, one may increase only one of these activities, and optionally also reduce the other activity (e.g., to generate an Fc region variant with improved ADCC activity, but reduced CDC activity and vice versa).

Fc mutations can also be introduced in the TNF-α binding molecules of the present invention to alter their interaction with the neonatal Fc receptor (FcRn) and improve their pharmacokinetic properties. Several experiments suggest that the interaction between the Fc region of an antibody and the FcRn plays a role in the persistence of immunoglobulins in serum. For instance, an unusually short serum half-life is observed for IgG molecules in mice that lack a functional FcRn. Fc mutations that improve binding to the FcRn appear to prolong serum half-life and, conversely, mutations in the rat FcRn that result in tighter IgG binding also improve serum half-life. A collection of human Fc variants with improved binding to the FcRn has also been described (Shields et al., (2001) High resolution mapping of the binding site on human IgG1 for FcγRI, FcγRII, FcγRIII, and FcRn and design of IgG1 variants with improved binding to the FcγR, J. Biol. Chem. 276:6591–6604). It has been reported that the increased binding affinity of IgG molecules for the FcRn observed at low pH (e.g., during pinocytosis or fluid phase endocytosis of IgG molecules from serum) impacts serum half-life (Ghetie et al., (1997) Increasing the serum persistence of an IgG fragment by random mutagenesis, Nat. Biotechnol. 15:637–640; Medesan et al., (1998) Comparative studies of rat IgG to further delineate the Fc:FcRn interaction site. Eur. J. Immunol. 28:2092–2100; Kim et al., (1999) Mapping the site on human IgG for binding of the MHC class I-related receptor, FcRn, Eur. J. Immunol. 29:2819–2825; Acqua et al., (2002) Increasing the affinity of a human IgG1 for the neonatal Fc receptor: biological consequences, J. Immunol. 169:5171–5180). However, mutations that increase binding at high pH appear to adversely affect serum half-life (Acqua et al., (2002) Increasing the affinity of a human IgG1 for the neonatal Fc receptor: biological consequences, J. Immunol. 169:5171–5180). All of the articles above are herein incorporated by reference. Therefore, Fc mutations could be introduced in the TNF-α binding molecules of the present invention in order to increase their affinity for the FcRn at low pH but maintain or decrease their affinity for the FcRn at higher pH.

Another type of amino acid substitution serves to alter the glycosylation pattern of the Fc region of a TNF-α binding molecule. This may be achieved, for example, by deleting one or more glycosylation site(s) found in the polypeptide, and/or adding one or more glycosylation sites that are not present in the polypeptide. Glycosylation of an Fc region is typically either N-linked or O-linked. N-linked refers to the attachment of the carbohydrate moiety to the side chain of an asparagine residue. The peptide sequences asparagine-X-serine and asparagine-X-threonine, where X is any amino acid except proline, are the recognition sequences for enzymatic attachment of the carbohydrate moiety to the asparagine side chain. Thus, the presence of either of these peptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the Fc region of a TNF-α binding molecule is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites).

In some embodiments, the present invention provides methods of treating a TNF-α mediated disease comprising the administration of the TNF-α binding molecules of the present invention to a subject (e.g., a human). In certain embodiments, the administration is under conditions such that the symptoms of the TNF-α mediated disease are reduced or eliminated. In particular embodiments, the TNF-α mediated disease is selected from sepsis, an autoimmune disease, rheumatoid arthritis, allergy, multiple sclerosis, autoimmune uveitis, nephrotic syndrome, an infectious disease, a malignancy, transplant rejection, graft-versus-host disease, systemic lupus erythematosus, thyroidosis, scleroderma, diabetes mellitus, Graves' disease, a pulmonary disorder, a bone disorder, an intestinal disorder, a cardiac disorder, cachexia, circulatory collapse, shock resulting from acute or chronic bacterial infections, acute and chronic parasitic and/or infectious diseases, chronic inflammatory pathologies, vascular inflammatory pathologies, sarcoidosis, inflammatory bowel disease, ulcerative colitis, Crohn's disease, disseminated intravascular coagulation, atherosclerosis, Kawasaki's pathology, neurodegenerative diseases, demyelinating diseases, multiple sclerosis, acute transverse myelitis, extrapyramidal and cerebellar disorders, lesions of the corticospinal system, disorders of the basal ganglia, hyperkinetic movement disorders, Huntington's chorea, senile chorea, drug-induced movement disorders (e.g., those induced by drugs which block CNS dopamine receptors), hypokinetic movement disorders, Parkinson's disease, progressive supranuclear palsy, spinocerebellar disorders, structural lesions of the cerebellum, spinocerebellar degenerations, spinal ataxia, Friedreich's ataxia, cerebellar cortical degenerations, multiple systems degenerations, Shy-Drager syndrome, Mencel, Dejerine-Sottas, and Machado-Joseph diseases, systemic disorders, Refsum's disease, abetalipoprotemia, ataxia, telangiectasia, mitochondrial multi-system disorder, disorders of the motor unit, neurogenic muscular atrophies, anterior horn cell degeneration, amyotrophic lateral sclerosis, infantile spinal muscular atrophy, juvenile spinal muscular atrophy, Alzheimer's disease, Down's Syndrome, Diffuse Lewy body disease, senile dementia of Lewy body type, Wernicke-Korsakoff syndrome, chronic alcoholism, Creutzfeldt-Jakob disease, subacute sclerosing panencephalitis, Hallerrorden-Spatz disease, dementia pugilistica, malignant pathologies involving TNF-α-secreting tumors or other malignancies involving TNF, such as, leukemias (acute, chronic myelocytic, chronic lymphocytic and/or myelodyspastic syndrome), lymphomas (e.g., Hodgkin's, non-Hodgkin's and Burkitt's lymphomas), mycosis fungoides, alcohol-induced hepatitis, psoriasis, psoriatic arthritis, Wegener's granulomatosis, ankylosing spondylitis, heart failure, reperfusion injury, chronic obstructive pulmonary disease, pulmonary fibrosis, and hepatitis C infection. In preferred embodiments, the TNF-α mediated disease is selected from the group consisting of juvenile and adult rheumatoid arthritis, Crohn's disease, psoriasis, ulcerative colitis, psoriatic arthritis, ankylosing spondylitis, and other spondyloarthropathies, Wegener's granulomatosis, idiopathic pulmonary fibrosis, chronic obstructive pulmonary disease, asthma, oncology, and graft-versus-host disease.

In some embodiments, the TNF-α binding molecule is administered in combination with an immunosuppressant such as methotrexate. In other embodiments, the TNF-α binding molecule is administered intravenously.

In certain embodiments, the present invention provides kits comprising: a) a TNF-α binding molecule of the present invention; and b) instructions for using the TNF-α binding molecule to treat a disease in a subject or instructions for employing the TNF-α binding molecule for scientific research or diagnostic purposes (e.g., for performing ELISA assays, etc.). In some embodiments, the present invention provides cell lines stably or transiently transfected with nucleic acid sequences encoding the TNF-α binding molecules of the present invention.

DESCRIPTION OF THE FIGURES

FIG. 1A shows the amino acid sequence of the light chain variable region of hu1 (SEQ ID NO: 1), and FIG. 1B shows the nucleic acid sequence of the light chain variable region of hu1 (SEQ ID NO: 2).

FIG. 2A shows the amino acid sequence of the heavy chain variable region of hu1 (SEQ ID NO: 3), and FIG. 2B shows the nucleic acid sequence of the heavy chain variable region of hu1 (SEQ ID NO: 4).

FIG. 3A shows the amino acid sequence of the light chain variable region of A10K (SEQ ID NO: 5), and FIG. 3B shows the nucleic acid sequence of the light chain variable region of A10K (SEQ ID NO: 6).

FIG. 4A shows the amino acid sequence of the heavy chain variable region of A10K (SEQ ID NO: 7), and FIG. 4B shows the nucleic acid sequence of the heavy chain variable region of A10K (SEQ ID NO: 8).

FIG. 5A shows the amino acid sequence of a fully human light chain framework region with interspersed CDRs. The four framework sub-regions are labeled as follows: FRL1 (SEQ ID NO: 57), FRL2 (SEQ ID NO: 58), FRL3 (SEQ ID NO: 59), and FRL4 (SEQ ID NO: 60). FIG. 5B shows the nucleic acid sequence of a fully human light chain framework region with interspersed CDRs. The four framework sub-regions are labeled as follows: FRL1 (SEQ ID NO: 61), FRL2 (SEQ ID NO: 62), FRL3 (SEQ ID NO: 63), and FRL4 (SEQ ID NO: 64).

FIG. 6A shows the amino acid sequence of a fully human heavy chain framework region with interspersed CDRs. The four framework sub-regions are labeled as follows: FRH1 (SEQ ID NO: 65), FRH2 (SEQ ID NO: 66), FRH3 (SEQ ID NO: 67), and FRH4 (SEQ ID NO: 68). FIG. 6B shows the nucleic acid sequence of a fully human heavy chain framework region with interspersed CDRs. The four framework sub-regions are labeled as follows: FRH1 (SEQ ID NO: 69), FRH2 (SEQ ID NO: 70), FRH3 (SEQ ID NO: 71), and FRH4 (SEQ ID NO: 72).

FIG. 14 shows the nucleic acid sequence of a human CL sequence, and a human CH1 sequence, that were used in the construction of the Fab fragments described in Example 1.

DEFINITIONS

Figure 7:
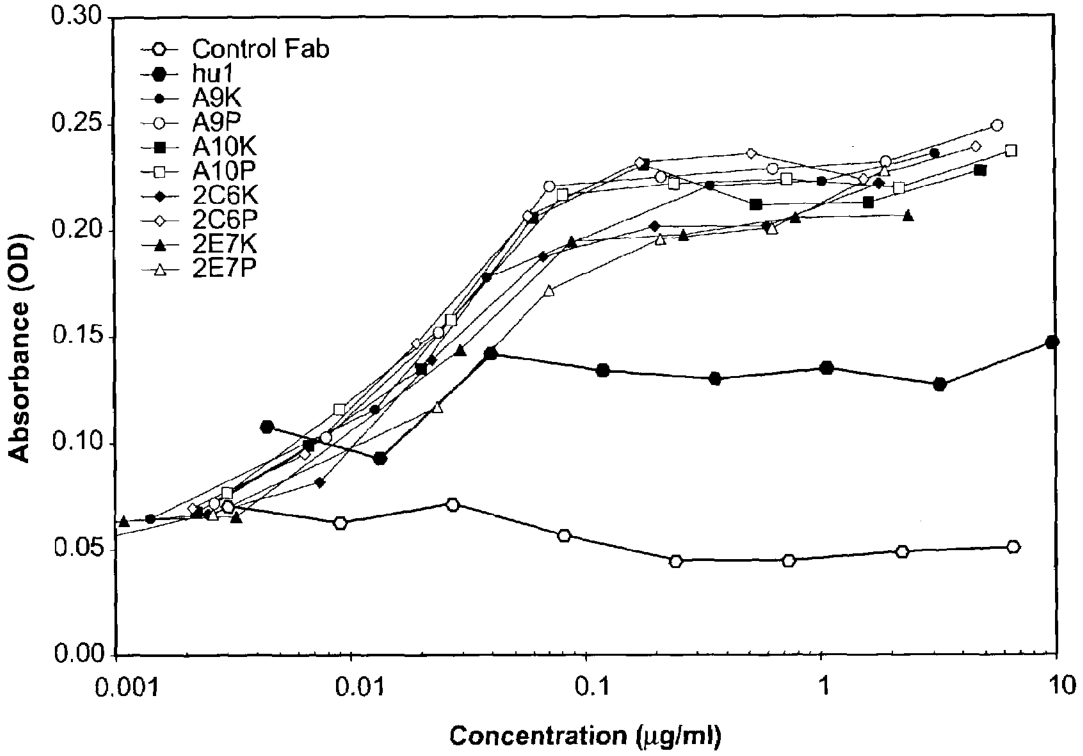
FIG. 7 shows the results of an ELISA described in Example 1.

To facilitate an understanding of the invention, a number of terms are defined below.

The term "antibody," as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3 (see FIG. 13). Each light chain is comprised of a light chain variable region (abbreviated herein as LCVR or VL) and a light chain constant region. The light chain constant region is comprised of one domain, CL (see FIG. 13). The VH and VL regions can be further subdivided into regions of hypervariability, termed complementarity determining regions (CDRs), interspersed with regions that are more conserved, termed framework regions (FR). Each variable region (VH or VL) contains 3 CDRs, designated CDR1, CDR2 and CDR3 (see FIGS. 5, 6, and 13). Each variable region also contains 4 framework sub-regions, designated FR1, FR2, FR3 and FR4 (see FIGS. 5, 6, and 13).

As used herein, the term "antibody fragments" refers to a portion of an intact antibody. Examples of antibody fragments include, but are not limited to, linear antibodies, single-chain antibody molecules, Fab and $F(ab')_2$ fragments, and multispecific antibodies formed from antibody fragments. The antibody fragments preferably retain at least part of the heavy and/or light chain variable region.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The residues that make up these six CDRs have been characterized by Kabat and Chothia as follows: residues 24–34 (CDRL1), 50–56 (CDRL2) and 89–97 (CDRL3) in the light chain variable region and 31–35 (CDRH1), 50–65 (CDRH2) and 95–102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26–32 (CDRL1), 50–52 (CDRL2) and 91–96 (CDRL3) in the light chain variable region and 26–32 (CDRH1), 53–55 (CDRH2) and 96–101 (CDRH3) in the heavy chain variable region; Chothia and Lesk (1987) J. Mol. Biol. 196: 901–917, herein incorporated by reference. Unless otherwise specified, the terms "complementarity determining region" and "CDR" as used herein, include the residues that encompass both the Kabat and Chothia definitions (i.e., residues 24–34 (CDRL1), 50–56 (CDRL2), and 89–97 (CDRL3) in the light chain variable region; and 26–35 (CDRH1), 50–65 (CDRH2), and 95–102 (CDRH3)). Also, unless specified, as used herein, the numbering of CDR residues is according to Kabat.

As used herein, the term "framework" refers to the residues of the variable region other than the CDR residues as defined herein. There are four separate framework sub-regions that make up the framework: FR1, FR2, FR3, and FR4 (See FIGS. 5, 6, and 13). In order to indicate if the framework sub-region is in the light or heavy chain variable region, an "L" or "H" may be added to the sub-region abbreviation (e.g., "FRL1" indicates framework sub-region 1 of the light chain variable region). Unless specified, the numbering of framework residues is according to Kabat.

As used herein, the term "fully human framework" means a framework with an amino acid sequence found naturally in humans. Examples of fully human frameworks, include, but are not limited to, KOL, NEWM, REI, EU, TUR, TEI, LAY and POM (See, e.g., Kabat et al., (1991) Sequences of Proteins of Immunological Interest, U.S. Department of Health and Human Services, NIH, USA; and Wu et al., (1970) J. Exp. Med. 132, 211–250, both of which are herein incorporated by reference).

As used herein, the terms "subject" and "patient" refer to any animal, such as a mammal like a dog, cat, bird, livestock, and preferably a human (e.g., a human with a TNF-α mediated disease).

As used herein, the terms "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage, Therefore, an end of an oligonucleotide or polynucleotide, is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "codon" or "triplet" refers to a group of three adjacent nucleotide monomers which specify one of the naturally occurring amino acids found in polypeptides. The term also includes codons which do not specify any amino acid.

As used herein, the terms "an oligonucleotide having a nucleotide sequence encoding a polypeptide," "polynucleotide having a nucleotide sequence encoding a polypeptide," and "nucleic acid sequence encoding a peptide" means a nucleic acid sequence comprising the coding region of a particular polypeptide. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Also, as used herein, there is no size limit or size distinction between the terms "oligonucleotide" and "polynucleotide." Both terms simply refer to molecules composed of nucleotides. Likewise, there is no size distinction between the terms "peptide" and "polypeptide." Both terms simply refer to molecules composed of amino acid residues.

As used herein, the terms "complementary" or "complementarity" are used in reference to polynucleotides (i.e., a sequence of nucleotides) related by the base-pairing rules. For example, the sequence "5'-A-G-T 3", is complementary to the sequence "3-T-C-A-5'". Complementarity may be "partial", in which only some of the nucleic acids' bases are matched according to the base pairing rules, or, there may be "complete" or "total" complementarity between the nucleic acids. The degree of complementarity between nucleic acid strands has significant effects on the efficiency and strength of hybridization. This is of particular importance in amplification reactions, as well as in detection methods that depend upon binding between nucleic acids.

As used herein, the term "the complement of" a given sequence is used in reference to the sequence that is completely complementary to the sequence over its entire length. For example, the sequence 5'-A-G-T-A-3' is "the complement" of the sequence 3'-T-C-A-T-5'. The present invention also provides the complement of the sequences described herein (e.g., the complement of the nucleic acid sequences in SEQ ID NOs: 1–84).

The term "homology" (when in reference to nucleic acid sequences) refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous".

The term "inhibition of binding", when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and the length and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent [50× Denhardt's contains per 500 ml: 5 g Ficoll (Type 400, Pharmacia), 5 g BSA (Fraction V; Sigma)] and 100 μg/ml denatured salmon sperm DNA, followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE, 0.5% SDS, 5× Denhardt's reagent and 100 μg/ml denatured salmon sperm DNA, followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE, 0.1% SDS, 5× Denhardt's reagent and 100 g/ml denatured salmon sperm DNA, followed by washing in a solution comprising 5×SSPE, 0.1% SDS at 42° C. when a probe of about 500 nucleotides in length is employed.

As used herein, the term "polymerase chain reaction" ("PCR") refers to the method described in U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repetitive aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

The term "isolated" when used in relation to a nucleic acid, as in "an isolated oligonucleotide" or "isolated polynucleotide" or "isolated nucleic acid sequence encoding a TNF-α binding molecule" refers to a nucleic acid sequence that is identified and separated from at least one contaminant nucleic acid with which it is ordinarily associated in its natural source. Isolated nucleic acid is present in a form or setting that is different from that in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.).

As used herein, the term "portion" when in reference to an amino acid sequence (as in "a portion of a given amino acid sequence") refers to fragments of that sequence. The fragments may range in size from six amino acids to the entire amino acid sequence minus one amino acid (e.g., 6 amino acids, 10, 20, 30, 40, 75, 200, etc.).

As used herein, the term "purified" or "to purify" refers to the removal of contaminants from a sample. For example, TNF-α specific antibodies may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial host cells and the polypeptides are purified by the removal of host cell proteins; the percentage of recombinant antigen-specific polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells such as PER.C6™ (Crucell, The Netherlands) and CHO cells, avian cells, amphibian cells, plant cells, fish cells, and insect cells), whether located in vitro or in vivo. For example, host cells may be located in a transgenic animal.

The terms "transfection" and "transformation" as used herein refer to the introduction of foreign DNA into cells (e.g., eukaryotic and prokaryotic cells). Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time, the foreign DNA is subject to the regulatory controls that govern the expression of endogenous genes in the chromosomes. The term "transient transfectant" refers to cells that have taken up foreign DNA but have failed to integrate this DNA.

As used herein, the terms "computer memory" and "computer memory device" refer to any storage media readable by a computer processor. Examples of computer memory include, but are not limited to, RAM, ROM, computer chips, digital video discs (DVDs), compact discs (CDs), hard disk drives (HDD), and magnetic tapes.

As used herein, the term "computer readable medium" refers to any device or system for storing and providing information (e.g., data and instructions) to a computer processor. Examples of computer readable media include, but are not limited to, DVDs, CDs, hard disk drives, magnetic tapes and servers for streaming media over networks.

As used herein, the phrase "computer readable medium encodes a representation" of a nucleic acid or amino acid sequence, refers to computer readable medium that has stored thereon information, that when delivered to a processor, allows the nucleic or amino acid sequence to be displayed to a user (e.g., printed out or presented on a display screen).

As used herein, the terms "processor" and "central processing unit" or "CPU" are used interchangeably and refer to a device that is able to read a program from a computer memory (e.g., ROM or other computer memory) and perform a set of steps according to the program.

Figure 13:
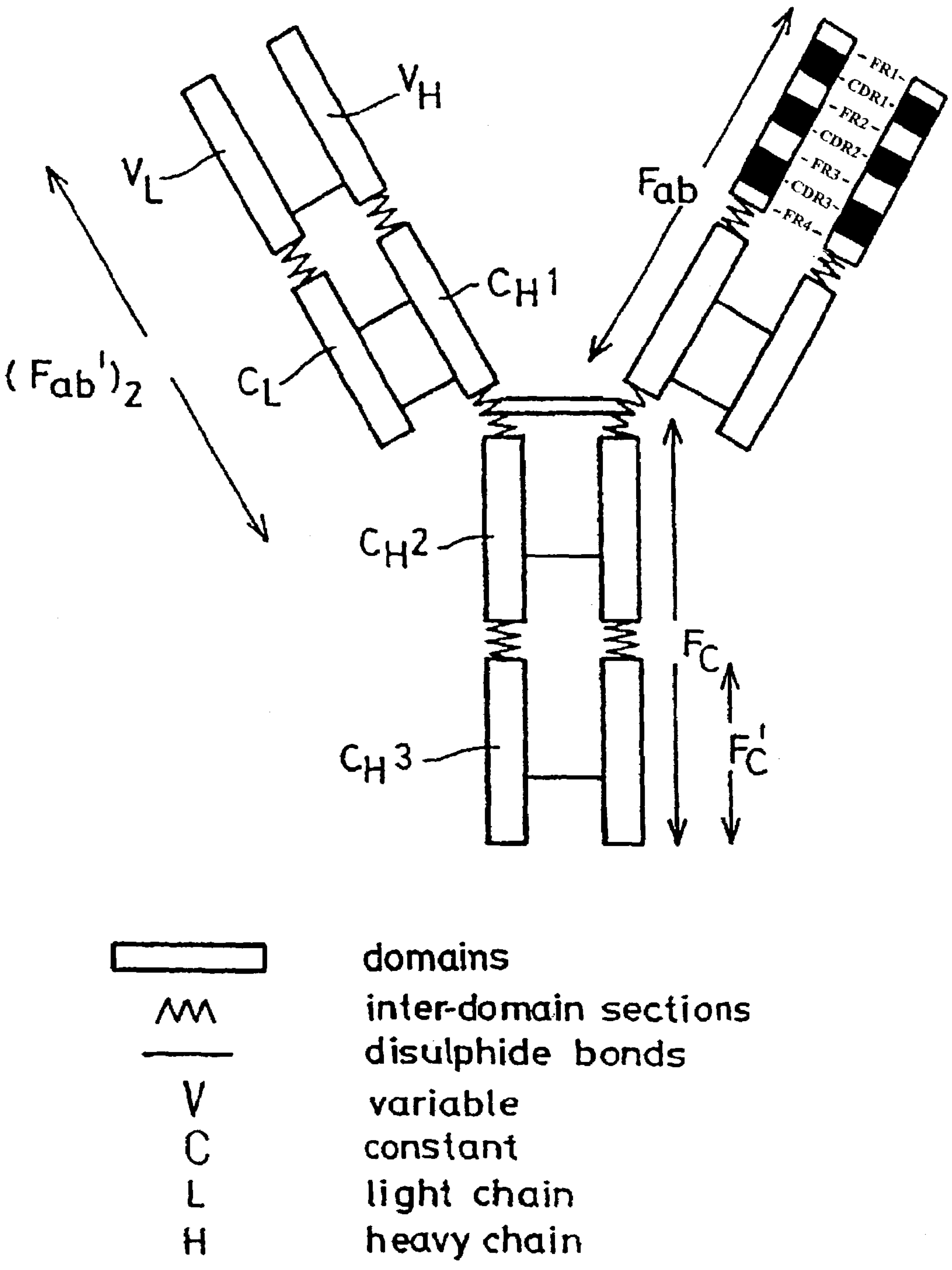
FIG. 13 shows a schematic representation of an IgG molecule with the various regions and sections labeled. The CDRs and framework regions (FR) of one of the two variable region light chains, and one of the two variable region heavy chains, are also labeled.

As used herein, the term "Fc region" refers to a C-terminal region of an immunoglobulin heavy chain (e.g., as shown in FIG. 13). The "Fc region" may be a native sequence Fc region or a variant Fc region (e.g., with increased or decreased effector functions).

As used herein, an Fc region may possess "effector functions" that are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g. Fc binding assays, ADCC assays, CDC assays, etc.).

As used herein, an "isolated" peptide, polypeptide, or protein is one that has been identified and separated and/or recovered from a component of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the isolated polypeptide is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or nonreducing conditions using Coomassie blue, or silver stain. An isolated polypeptide includes the polypeptide in situ within recombinant cells since at least one component of the polypeptide's natural environment will not be present. Ordinarily, however, an isolated polypeptide will be prepared by a least one purification step.

As used herein, the term "treatment" refers to both therapeutic treatment and prophylactic or preventative measures. Those in need of treatment include those already with the disorder as well as those in which the disorder is to be prevented.

As used herein, nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. In preferred embodiments, "operably linked" means that the DNA sequences being linked are contiguous, and, in the case of a secretory leader, contiguous and in reading frame. However, enhancers, for example, do not have to be contiguous. Linking may be accomplished, for example, by ligation at convenient restriction sites. If such sites do not exist, synthetic oligonucleotide adaptors or linkers may be used in accordance with conventional practice.

The phrase "under conditions such that the symptoms are reduced" refers to any degree of qualitative or quantitative reduction in detectable symptoms of any TNF-α mediated disease, including but not limited to, a detectable impact on the rate of recovery from disease (e.g., rate of weight gain), or the reduction of at least one of the symptoms normally associated with the particular disease (e.g., if the TNF-α mediated disease were Crohn's disease, a reduction in at least one of the following symptoms: abdominal pain, diarrhea, rectal bleeding, weight loss, fever, loss of appetite, dehydration, anemia, distention, fibrosis, inflamed intestines and malnutrition).

The term "human TNF-α" (abbreviated herein as hTNF-α, or simply hTNF), as used herein, is intended to refer to a human cytokine that exists as a 17 kDa secreted form and a 26 kDa membrane associated form, the biologically active form of which is composed of a trimer of noncovalently bound 17 kDa molecules. The structure of hTNF-α is described further in, for example, Jones, et al. (1989) Nature, 338:225–228. The term human TNF-α is intended to include recombinant human TNF-α (rhTNF-α), which can be prepared by standard recombinant expression methods or purchased commercially.

The terms "affinity", "binding affinity" and "$K_d$" refer to the equilibrium dissociation constant (expressed in units of concentration) associated with each TNF-α binding molecule—TNF-α protein complex. The binding affinity is directly related to the ratio of the off-rate constant (generally reported in units of inverse time, e.g., $seconds^{-1}$) to the on-rate constant (generally reported in units of concentration per unit time, e.g., molar/second). The binding affinity may be determined by, for example, a kinetic exclusion assay or surface plasmon resonance.

The terms "dissociation", "dissociation rate" and "$k_{off}$" as used herein, are intended to refer to the off rate constant for dissociation of a TNF-α binding molecule from the antibody/antigen complex.

The terms "association", "association rate" and "$k_0$," as used herein, are intended to refer to the on rate constant for association of a TNF-α binding molecule with an antigen to form an antibody/antigen complex.

The terms "effective concentration" and "$EC_{50}$" as used herein, are intended to refer to the concentration of a TNF-α binding molecule capable of interacting with, and neutralizing sufficient quantities of TNF-α molecules to produce an effect on approximately 50% of the treated cells. For example, in an L929 assay (See Example 2), the $EC_{50}$ is the concentration necessary to protect approximately 50% of the cells from TNF-α mediated cytotoxicity. In these assays, the concentration of TNF-α used is empirically determined in order to exert a cytotoxic effect on≧than 90% of the cell population. Also, herein, no distinction is made between effective ($EC_{50}$) and inhibitory ($IC_{50}$) concentration.

DESCRIPTION OF THE INVENTION

The present invention provides TNF-α binding molecules and nucleic acid sequences encoding TNF-α binding molecules. In particular, the present invention provides TNF-α binding molecules with a high binding affinity, a high association rate, a low dissociation rate with regard to human TNF-α and a low $EC_{50}$ value (e.g., in an L929 cell assay). Preferably, the TNF-α binding molecules of the present invention comprise light and/or heavy chain variable regions with fully human frameworks. In particularly preferred embodiments, the TNF-α binding molecules of the present invention comprise light and/or heavy chain variable regions with human germline frameworks. The description of the invention is divided into the following sections below for convenience: I. TNF-α Binding Molecules; II. Generating TNF-α Binding Molecules; III. Therapeutic Formulations and Uses; and IV. Additional TNF-α Binding Molecule Uses.

I. TNF-α Binding Molecules

The present invention provides TNF-α binding molecules with desirable characteristics. In particular, in some embodiments, the TNF-α binding molecules have a high binding affinity ($K_d$) with regard to human TNF-α. In other embodiments, the TNF-α binding molecules have a high association rate constant ($k_{on}$) with regard to human TNF-α. In certain embodiments, the TNF-α binding molecules have a low dissociation rate ($k_{off}$) with regard to human TNF-α. In other embodiments, the TNF-α binding molecules have a low effective concentration ($EC_{50}$) in cell-based assays. In preferred embodiments, the TNF-α binding molecules of the present invention have a high binding affinity, a high association rate, a low dissociation rate and are effective at a low concentrations. While not necessary to practice or understand the invention, it is believed that the TNF-α binding molecules of the present invention, with high binding affinity, a high association rate, a low dissociation rate and a low $EC_{50}$, are particularly well suited for therapeutic use in humans (e.g., for treating TNF-α mediated diseases).

In further embodiments, the TNF-α binding molecules of the present invention do not bind murine TNF-α. In other embodiments, the TNF-α binding molecules of the present invention do not bind rat, pig, or rhesus macaque TNF-α.

In preferred embodiments, the TNF-α binding molecules of the present invention comprise a light and/or heavy chain variable region, preferably having a fully human framework. In particularly preferred embodiments, the TNF-α binding molecules of the present invention comprise a light and/or heavy chain variable region, preferably having a human germline framework. While not necessary to practice or understand the invention, it is believed that the TNF-α binding molecules of the present invention (see, e.g. the Examples below) will illicit very little or no immunogenic response when administered to a human (e.g. to treat a disease).

As described below in Tables 1, 2 and 3, the present invention provides numerous CDRs useful for generating TNF-α binding molecules. For example, one or more of the CDRs shown can be combined with a framework sub-region (e.g., a fully human FR1, FR2, FR3, or FR4) in order to generate a TNF-α binding peptide, or a nucleic acid sequence encoding a TNF-α binding peptide. Also, the CDRs shown in the Tables below may be combined, for example, such that three CDRs are present in a light chain variable region, and/or three CDRs are present in a heavy chain variable region.

The CDRs shown below may be inserted into a human framework (by recombinant techniques) into the light and heavy chain frameworks shown in FIGS. 5 and 6 in order to generate TNF-α binding molecules or nucleic acid sequences encoding TNF-α binding molecules. For example, the CDRL1 shown in FIG. 5A could be replaced by SEQ ID NO: 9, 11, 13, 15, or 17 as shown in Table 1. Likewise, the CDRL1 shown in FIG. 5B could be replaced by SEQ ID NO: 10, 12, 14, 16, or 18 and shown in Table 1. This same procedure may be used with all of the CDRs shown in Tables 1–3. These three tables are show immediately below.

TABLE 1

Light Chain CDRs

| SEQ ID NO | CDR Name* | change from hu1** | Sequence |
|---|---|---|---|
| SEQ ID NO:9 | CDRL1 | none | RASQFVGSSIH |
| SEQ ID NO:10 | CDRL1 | none | AGGGCCAGTCAGTTCGTTGGCTCAAGCATCCAC |
| SEQ ID NO:11 | CDRL1 | S31L | RASQFVGLSIH |

TABLE 1-continued

Light Chain CDRs

| SEQ ID NO | CDR Name* | change from hu1** | Sequence |
|---|---|---|---|
| SEQ ID NO:12 | CDRL1 | S31L | AGGGCCAGTCAGTTCGTTGGCCTTAGCATCCAC |
| SEQ ID NO:13 | CDRL1 | S31M | RASQFVGMSIH |
| SEQ ID NO:14 | CDRL1 | S31M | AGGGCCAGTCAGTTCGTTGGCATGAGCATCCAC |
| SEQ ID NO:15 | CDRL1 | S31Y | RASQFVGYSIH |
| SEQ ID NO:16 | CDRL1 | S31Y | AGGGCCAGTCAGTTCGTTGGCTATAGCATCCAC |
| SEQ ID NO:17 | CDRL1 | S31Xaa | RASQFVGXaaSIH |
| SEQ ID NO:18 | CDRL1 | S31Xaa | AGGGCCAGTCAGTTCGTTGGCnnnAGCATCCAC |
| SEQ ID NO:19 | CDRL2 | none | YASESMS |
| SEQ ID NO:20 | CDRL2 | none | TATGCTTCTGAGTCTATGTCT |
| SEQ ID NO:21 | CDRL2 | S54Y | YASEYMS |
| SEQ ID NO:22 | CDRL2 | S54Y | TATGCTTCTGAGTATATGTCT |
| SEQ ID NO:23 | CDRL2 | S54Xaa | YASEXaaMS |
| SEQ ID NO:24 | CDRL2 | S54Xaa | TATGCTTCTGAGnnnATGTCT |
| SEQ ID NO:25 | CDRL2 | M55R | YASESRS |
| SEQ ID NO:26 | CDRL2 | M55R | TATGCTTCTGAGTCTAGGTCT |
| SEQ ID NO:27 | CDRL2 | M55K | YASESKS |
| SEQ ID NO:28 | CDRL2 | M55K | TATGCTTCTGAGTCTAAGTCT |
| SEQ ID NO:29 | CDRL2 | M55Xaa | YASESXaaS |
| SEQ ID NO:30 | CDRL2 | M55Xaa | TATGCTTCTGAGTCTnnnTCT |
| SEQ ID NO:31 | CDRL2 | S54Xaa and M55Xaa | YASEXaaXaaS |
| SEQ ID NO:32 | CDRL2 | S54Xaa and M55Xaa | TATGCTTCTGAGnnnnnnTCT |
| SEQ ID NO:33 | CDRL3 | none | QQSHSWHFT |
| SEQ ID NO:34 | CDRL3 | none | CAACAAAGTCATAGCTGGCATTTCACG |

*The work of Kabat was used to number residues. CDRs include Kabat and Chothia residues.
**Changes from hu1 are designated by the hu1 amino acid, followed by the position, and then the new amino acid (e.g., S31L is a change from S at position 31 to L).
***"Xaa" indicates this position can be any amino acid, and "n" indicates this position can be any nucleotide.

TABLE 2

Heavy Chain CDRs

| SEQ ID NO | CDR Name* | change from hu1** | Sequence*** |
|---|---|---|---|
| SEQ ID NO:35 | CDRH1 | none | GFTFSNHWMN |
| SEQ ID NO:36 | CDRH1 | none | GGATTCACTTTCAGTAACCACTGGATGAAC |
| SEQ ID NO:37 | CDRH1 | T28K | GFKFSNHWMN |
| SEQ ID NO:38 | CDRH1 | T28K | GGATTCAAGTTCAGTAACCACTGGATGAAC |
| SEQ ID NO:39 | CDRH1 | T28P | GFPFSNHWMN |

TABLE 2-continued

Heavy Chain CDRs

| SEQ ID NO | CDR Name* | change from hu1** | Sequence*** |
|---|---|---|---|
| SEQ ID NO:40 | CDRH1 | T28P | GGATTCCCTTTCAGTAACCACTGGATGAAC |
| SEQ ID NO:41 | CDRH1 | T28Xaa | GFXaaFSNHWMN |
| SEQ ID NO:42 | CDRH1 | T28Xaa | GGATTCnnnTTCAGTAACCACTGGATGAAC |
| SEQ ID NO:43 | CDRH2 | none | EIRSKSINSATHYAESVKG |
| SEQ ID NO:44 | CDRH2 | none | GAAATTAGATCAAAATCTATTAATTCTGCAACACAT TATGCGGAGTCTGTGAAAGGG |
| SEQ ID NO:45 | CDRH2 | I53M | EIRSKSMNSATHYAESVKG |
| SEQ ID NO:46 | CDRH2 | I53M | GAAATTAGATCAAAATCTATGAATTCTGCAACACA TTATGCGGAGTCTGTGAAAGGG |
| SEQ ID NO:47 | CDRH2 | I53Xaa | EIRSKSXaaNSATHYAESVKG |
| SEQ ID NO:48 | CDRH2 | I53Xaa | GAAATTAGATCAAAATCTnnnAATTCTGCAACACATT ATGCGGAGTCTGTGAAAGGG |
| SEQ ID NO:49 | CDRH2 | E61R | EIRSKSINSATHYARSVKG |
| SEQ ID NO:50 | CDRH2 | E61R | GAAATTAGATCAAAATCTATTAATTCTGCAA CACATTATGCGCGTTCTGTGAAAGGG |
| SEQ ID NO:51 | CDRH2 | E61Xaa | EIRSKSINSATHYAXaaSVKG |
| SEQ ID NO:52 | CDRH2 | E61Xaa | GAAATTAGATCAAAATCTATTAATTCTGCAACAC ATTATGCGnnnTCTGTGAAAGGG |
| SEQ ID NO:55 | CDRH2 | I53M + E61R | EIRSKSMNSATHYARSVKG |
| SEQ ID NO:56 | CDRH2 | I53M + E61R | GAAATTAGATCAAAATCTATGAATTCTGCAAC ACATTATGCGCGTTCTGTGAAAGGG |
| SEQ ID NO:53 | CDRH3 | none | NYYGSTYDH |
| SEQ ID NO:54 | CDRH3 | none | AATTACTACGGTAGTACCTACGACCAT |

*The work of Kabat was used to number residues. CDRs include both Kabat and Chothia residues.
**Changes from hu1 are designated by the hu1 amino acid, followed by the position, and then the new amino acid (e.g., T28K is a change from T at position 28 to K).
***"Xaa" indicates this position can be any amino acid, and "n" indicates this position can be any nucleotide.

TABLE 3

Additional beneficial CDRs

| SEQ ID NO:73 | CDRL1 | S26P | RAPQFVGSSIH |
|---|---|---|---|
| SEQ ID NO:74 | CDRL1 | S26P | AGGGCCCCTCAGTTCGTTGGCTCAAGCATCCAC |
| SEQ ID NO:75 | CDRL1 | S26Xaa | RAXaaQFVGSSIH |
| SEQ ID NO:76 | CDRL1 | S26Xaa | AGGGCCnnnCAGTTCGTTGGCTCAAGCATCCAC |
| SEQ ID NO:77 | CDRL1 | G30Y | RASQFVYSSIH |
| SEQ ID NO:78 | CDRL1 | G30Y | AGGGCCAGTCAGTFTCGTTTATTCAAGCATCCAC |
| SEQ ID NO:79 | CDRL1 | G30Xaa | RASQFVXaaSSIH |
| SEQ ID NO:80 | CDRL1 | G30Xaa | AGGGCCAGTCAGTTCGTTnnnTCAAGCATCCAC |
| SEQ ID NO:81 | CDRL3 | S93W | QQSHWWHFT |
| SEQ ID NO:82 | CDRL3 | S93W | CAACAAAGTCATTGGTGGCATTTCACG |

TABLE 3-continued

| Additional beneficial CDRs | | | |
|---|---|---|---|
| SEQ ID NO:83 | CDRL3 | S93Xaa | QQSHXaaWHFT |
| SEQ ID NO:84 | CDRL3 | S93Xaa | CAACAAAGTCATnnnTGGCATTTCACG |

*The work of Kabat was used to number residues. CDRs include both Kabat and Chothia residues.
**Changes from hu1 are designated by the hu1 amino acid, followed by the position, and then the new amino acid (e.g., T28K is a change from T at position 28 to K)
***"Xaa" indicates this position can be any amino acid, and "n" indicates this position can be any nucleotide.

The present invention also provides sequences that are substantially the same as the CDR sequences (both amino acid and nucleic acid) shown in the above Tables For example, one or two amino acid may be changed in the sequences shown in the Tables. Also for example, a number of nucleotide bases may be changed in the sequences shown in the Tables. Changes to the amino acid sequence may be generated by changing the nucleic acid sequence encoding the amino acid sequence. A nucleic acid encoding a variant of a given CDR may be prepared by methods known in the art using the guidance of the present specification for particular sequences. These methods include, but are not limited to, preparation by site-directed (or oligonucleotide-mediated) mutagenesis, PCR mutagenesis, and cassette mutagenesis of an earlier prepared nucleic acid encoding the CDR. Site-directed mutagenesis is a preferred method for preparing substitution variants. This technique is well known in the art (see, e.g., Carter et al., (1985) Nucleic Acids Res. 13: 4431–4443 and Kunkel et. al., (1987) Proc. Natl. Acad. Sci. U.S.A 82: 488–492, both of which are hereby incorporated by reference).

Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting CDR (see, e.g., Vallette et. al., (1989) Nucleic Acids Res. 17: 723–733, hereby incorporated by reference). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., (1985) Gene 34: 315–323, hereby incorporated by reference. The starting material is the plasmid (or other vector) comprising the starting CDR DNA to be mutated. The codon(s) in the starting DNA to be mutated are identified. There should be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant can be determined, and a nucleic acid sequence encoding such amino acid sequence variant can be generated synthetically. Conservative modifications in the amino acid sequences of the CDRs may also be made. Naturally occurring residues are divided into classes based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions will entail exchanging a member of one of these classes for another member of the same class. The present invention also provides the complement of the nucleic acid sequences shown in Tables 1–3, as well as nucleic acid sequences that will hybridize to these nucleic acid sequences under low, medium, and high stringency conditions.

The CDRs of the present invention may be employed with any type of framework. Preferably, the CDRs are used with fully human frameworks, or framework sub-regions. In particularly preferred embodiments, the frameworks are human germline sequences. One example of a fully human framework is shown in FIGS. 5 and 6. Other fully human frameworks or framework sub-regions may also be employed. For example, the NCBI web site contains the sequences for the currently known human framework regions. Examples of human VH sequences include, but are not limited to, VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, Vh3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81, which are provided in Matsuda et al., (1998) J. Exp. Med. 188:1973–1975, that includes the complete nucleotide sequence of the human immunoglobulin chain variable region locus, herein incorporated by reference. Examples of human VK sequences include, but are not limited to, A1, A10, A11, A14, A17, A18, A19, A2, A20, A23, A26, A27, A3, A30, A5, A7, B2, B3, L1, L10, L1, L12, L14, L15, L16, L18, L19, L2, L20, L22, L23, L24, L25, L4/18a, L5, L6, L8, L9, O1, O11, O12, O14, O18, O2, O4, and O8, which are provided in Kawasaki et al., (2001) Eur. J. Immunol. 31:1017–1028; Schable and Zachau, (1993) Biol. Chem. Hoppe Seyler 374:1001–1022; and Brensing-Kuppers et al., (1997) Gene 191:173–181, all of which are herein incorporated by reference. Examples of human VL sequences include, but are not limited to, V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-4, V4-6, V5-1, V5-2, V5-4, and V5-6, which are provided in Kawasaki et al., (1997) Genome Res. 7:250–261, herein incorporated by reference. Fully human frameworks can be selected from any of these functional germline genes. Generally, these frameworks differ from each other by a limited number of amino acid changes. These frameworks may be used with the CDRs described herein. For example, L6, a frequently used gene among the Vk3 sub-family could be selected as an alternate framework for the light chain of the TNF-α binding molecules of the present invention. Additional examples of human frameworks which may be used with the CDRs of the present invention include, but are not limited to, KOL, NEWM, REI, EU, TUR, TEI, LAY and POM (See, e.g., Kabat et al., (1991) Sequences of Proteins of Immunological Interest, U.S. Department of Health and Human Services, NIH, U.S.A; and Wu et al., (1970), J. Exp. Med. 132:211–250, both of which are herein incorporated by reference).

Again, while not necessary to practice or understand the invention, it is believed that the reason the use of germline sequences is expected to help eliminate adverse immune responses in most individuals is as follows. Somatic mutations frequently occur in the variable region of immunoglobulins as a result of the affinity maturation step that takes place during a normal immune response. Although these mutations are predominantly clustered around the hypervariable CDRs, they also impact residues in the framework regions. These framework mutations are not present in the germline genes and are likely to be immunogenic in patients. In contrast, the general population has been exposed to the vast majority of framework sequences expressed from germline genes and, as a result of immunologic tolerance, these germline frameworks are expected to be less, or non-immunogenic in patients. In order to maximize the likelihood of tolerance, genes encoding the variable regions can be selected from a collection of commonly occurring, functional germline genes, and genes encoding VH and VL regions can be further selected to match known associations between specific heavy and light chains of immunoglobulin molecules.

II. Generating TNF-α Binding Molecules

In preferred embodiments, the TNF-α binding molecules of the present invention comprise antibodies or antibody fragments (e.g., comprising one or more of the CDRs described herein). An antibody, or antibody fragment, of the present invention can be prepared by recombinant expression of immunoglobulin light and heavy chain genes in a host cell. For example, to express an antibody recombinantly, a host cell may be transfected with one or more recombinant expression vectors carrying DNA fragments encoding the immunoglobulin light and heavy chains of the antibody such that the light and heavy chains are expressed in the host cell and, preferably, secreted into the medium in which the host cell is cultured, from which medium the antibody can be recovered. Standard recombinant DNA methodologies may be used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al., all of which are herein incorporated by reference.

To express an antibody with one or more of the CDRs of the present invention, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see above).

Once the germline VH and VL fragments are obtained, these sequences can be mutated to encode one or more of the CDR amino acid sequences disclosed herein (see, e.g., Tables 1–3). The amino acid sequences encoded by the germline VH and VL DNA sequences may be compared to the CDRs sequence(s) desired to identify amino acid residues that differ from the germline sequences. Then the appropriate nucleotides of the germline DNA sequences are mutated such that the mutated germline sequence encodes the selected CDRs (e.g., the six CDRs that are selected from Tables 1–3), using the genetic code to determine which nucleotide changes should be made. Mutagenesis of the germline sequences may be carried out by standard methods, such as PCR-mediated mutagenesis (in which the mutated nucleotides are incorporated into the PCR primers such that the PCR product contains the mutations) or site-directed mutagenesis. In other embodiments, the variable region is synthesized de novo (e.g., using a nucleic acid synthesizer).

Once DNA fragments encoding the desired VH and VL segments are obtained (e.g., by amplification and mutagenesis of germline VH and VL genes, or synthetic synthesis, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operably linked to another DNA fragment encoding another polypeptide, such as an antibody constant region or a flexible linker. The isolated DNA encoding the VH region can be converted to a full-length heavy chain gene by operably linking the VH-encoding DNA to another DNA molecule encoding heavy chain constant regions (CH1, CH2 and CH3). The sequences of human heavy chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be, for example, an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operably linked to another DNA molecule encoding only the heavy chain CH1 constant region.

The isolated DNA encoding the VL region can be converted to a full-length light chain gene (as well as a Fab light chain gene) by operably linking the VL-encoding DNA to another DNA molecule encoding the light chain constant region, CL. The sequences of human light chain constant region genes are known in the art (see e.g., Kabat, E. A., et al., (1991) Sequences of Proteins of immunological Interest, Fifth Edition, U.S. Department of Health and Human Services. NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH-and VL-encoding DNA fragments may be operably linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al., (1988) Science 242:423–426; Huston et al., (1988) Proc. Natl. Acad. Sci. U.S.A 85:5879–5883; McCafferty et al., (1990) Nature 348:552–554), all of which are herein incorporated by reference).

To express the antibodies, or antibody fragments of the invention, DNAs encoding partial or full-length light and heavy chains, obtained as described above, may be inserted into expression vectors such that the genes are operably linked to transcriptional and translational control sequences. In this context, the term "operably linked" is intended to mean that an antibody gene is ligated into a vector such that transcriptional and translational control sequences within the vector serve their intended function of regulating the transcription and translation of the antibody gene. The expression vector and expression control sequences are generally chosen to be compatible with the expression host cell used. The antibody light chain gene and the antibody heavy chain gene can be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). Prior to insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operably linked to the CH segment(s) within the vector and the VL segment is operably linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990), herein incorporated by reference. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma virus. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., all of which are herein incorporated by reference.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634.665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neomycin gene (for G418 selection).

For expression of the light and heavy chains, the expression vector(s) encoding the heavy and light chains may be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAF-dextran transfection and the like.

Preferred mammalian host cells for expressing the recombinant antibodies of the invention include PER.C6™ cells (Crucell, The Netherlands), Chinese Hamster Ovary (CHO cells) (including dhfr-CHO cells, described in Urlaub and Chasin, (1980) Proc. Natl. Acad. Sci. U.S.A 77:4216–4220, used with a DHFR selectable marker, e.g., as described in R. J. Kaufman and P. A. Sharp (1982) Mol. Biol. 159:601–621), NSO myeloma cells, COS cells and SP2 cells. When recombinant expression vectors encoding antibody genes are introduced into mammalian host cells, the antibodies are generally produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain of an antibody of this invention. Recombinant DNA technology may also be used to remove some or all of the DNA encoding either or both of the light and heavy chains that is not necessary for binding to hTNF-α. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNF-α by crosslinking an antibody of the invention to a second antibody by standard chemical crosslinking methods.

In one preferred system for recombinant expression of an antibody, or fragment thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector may also carry a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In certain embodiments, the antibodies and antibody fragments of the present invention are produced in transgenic animals. For example, transgenic sheep and cows may be engineered to produce the antibodies or antibody fragments in their milk (see, e.g., Pollock D P, et al., (1999) Transgenic milk as a method for the production of recombinant antibodies. J. Immunol. Methods 231:147–157, herein incorporated by reference). The antibodies and antibody fragments of the present invention may also be produced in plants (see, e.g., Larrick et al., (2001) Production of secretory IgA antibodies in plants. Biomol. Eng. 18:87–94, herein incorporated by reference). Additional methodologies and purification protocols are provided in Humphreys et al., (2001) Therapeutic antibody production technologies: molecules applications, expression and purification, Curr. Opin. Drug Discov. Devel. 4:172–185, herein incorporated by reference. In certain embodiments, the antibodies or antibody fragments of the present invention are produced by transgenic chickens (see, e.g., U.S. Pat. Pub. Nos. 20020108132 and 20020028488, both of which are herein incorporated by reference).

III. Therapeutic Formulations and Uses

The TNF-α binding molecules of the present invention (e.g. antibodies and antibody fragments) are useful for treating a subject having a pathology or condition associated with abnormal levels of a substance reactive with a TNF-α binding molecule, such as TNF-α in excess of, or less than, levels present in a normal healthy subject, where such excess or diminished levels occur in a systemic, localized or particular tissue type or location in the body. Such tissue types can include, but are not limited to, blood, lymph, CNS, liver, kidney, spleen, heart muscle or blood vessels, brain or spinal cord, white matter or gray matter, cartilage, ligaments, tendons, lung, pancreas, ovary, testes, and prostate. Increased or decreased TNF-α concentrations relative to normal levels can also be localized to specific regions or cells in the body, such as joints, synovium, nerve blood vessel junctions, bones, specific tendons or ligaments, or sites of infection, such as bacterial or viral infections.

TNF-related pathologies include, but are not limited to, the following:

(A) acute and chronic immune and autoimmune pathologies, such as systemic lupus erythematosus (SLE), rheumatoid arthritis, thyroidosis, graft-versus-host disease, scleroderma, diabetes mellitus, Graves' disease, and the like;

(B) sepsis, cachexia, circulatory collapse and/or shock resulting from acute or chronic bacterial, viral parasitic or fungal infections;

(C) inflammatory diseases, such as chronic inflammatory pathologies and vascular inflammatory pathologies, including chronic inflammatory pathologies such as, but not limited to, sarcoidosis, inflammatory bowel disease (i.e., ulcerative colitis and Crohn's disease) and vascular inflammatory pathologies, such as, but not limited to, disseminated intravascular coagulation, atherosclerosis, and Kawasaki's pathology;

(D) neurodegenerative diseases, including, but not limited to, demyelinating diseases, such as multiple sclerosis and acute transverse myelitis; extrapyramidal and cerebellar disorders such as lesions of the corticospinal system; disorders of the basal ganglia; hyperkinetic movement disorders such as Huntington's disease and senile chorea; drug-induced movement disorders, such as those induced by drugs which block CNS dopamine receptors; hypokinetic movement disorders, such as Parkinson's disease; progressive supranuclear palsy; cerebellar and spinocerebellar disorders, such as structural lesions of the cerebellum; spinocerebellar degenerations (spinal ataxia, Friedreich's ataxia, cerebellar cortical degenerations, multiple systems degenerations (Shy-Drager syndrome, Dejerine-Sottas, and Machado-Joseph diseases)); and systemic disorders (Refsum's disease, ataxia, telangiectasia, and mitochondrial multi.system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and dementia pugilistica, or any subset thereof;

(E) malignant pathologies involving TNF-secreting tumors or other malignancies involving TNF, such as, but not limited to leukemias (acute, chronic myelocytic, chronic lymphocytic and/or myclodyspastic syndrome); lymphomas (Hodgkin's and non-Hodgkin's lymphomas, such as malignant lymphomas (Burkitt's lymphoma or mycosis fungoides)); and (F) alcohol-induced hepatitis.

Additional TNF-α pathologies include, but are limited to, psoriasis, psoriatic arthritis, Wegener's granulomatosis, ankylosing spondylitis, heart failure, reperfusion injury, chronic obstructive pulmonary disease, pulmonary fibrosis, and hepatitis C infection. See, e.g., Berkow et al., eds., The Merck Manual, 16th edition, chapter 11, pp 1380–1529, Merck and Co., Rahway, N.J., 1992, herein incorporated by reference.

The TNF-α binding molecules of the present invention may be administered by any suitable means, including parenteral, non-parenteral, subcutaneous, topical, intraperitoneal, intrapulmonary, intranasal, and intralesional administration (e.g., for local immunosuppressive treatment). Parenteral infusions include, but are not limited to, intramuscular, intravenous, intra-arterial, intraperitoneal, or subcutaneous administration. In addition, TNF-α binding molecules are suitably administered by pulse infusion, particularly with declining doses. Preferably, the dosing is given by injections, most preferably intravenous or subcutaneous injections, depending in part on whether the administration is brief or chronic.

Dosage regimens may be adjusted to provide the optimum desired response (e g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the TNF-α binding molecules of the present invention are generally dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody fragment (or other TNF-α binding molecule of the invention) is 0.1–20 mg/kg, more preferably 1–10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the present invention.

The dosage administered will, of course, vary depending upon known factors such as the pharmacodynamic characteristics of the particular agent, its mode and route of administration, the age, health, and weight of the recipient, the nature and extent of symptoms, the kind of concurrent treatment, the frequency of treatment, and the effect desired. For example, a daily dosage of active ingredient can be about 0.01 to 100 milligrams per kilogram of body weight. Ordinarily 1.0 to 5, and preferably 1 to 10 milligrams per kilogram per day given in divided doses 1 to 6 times a day or in sustained release form, is effective to obtain desired results.

As a non-limiting example, treatment of TNF-related pathologies in humans or animals can be provided as a daily dosage of a TNF-α binding molecule of the present invention of 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof.

Dosage forms (compositions) suitable for internal administration generally contain from about 0.1 milligram to about 500 milligrams of active ingredient per unit. In these pharmaceutical compositions the active ingredient will ordinarily be present in an amount of about 0.5–95% by weight based on the total weight of the composition.

The TNF-α binding molecules of the invention can be incorporated into pharmaceutical compositions suitable for administration to a subject. For example, the pharmaceutical composition may comprise a TNF-α binding molecule (e.g. an antibody or antibody fragment) and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the TNF-α binding molecules.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson. ed., Marcel Dekker, Inc., New York, 1978).

In certain embodiments, the TNF-α binding molecules of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a TNF-α binding molecule (e.g. an antibody or antibody fragment) of the invention is coformulated with and/or coadministered with one or more additional therapeutic agents that are useful for treating disorders in which TNF-α activity is detrimental. For example, a TNF-α binding molecule of the invention may be coformulated and/or coadministered with one or more antibodies that bind other targets (e.g., antibodies that bind other cytokines or that bind cell surface molecules), one or more cytokines, soluble TNF-α receptor (see e.g., PCT Publication No. WO 94/06476) and/or one or more chemical agents that inhibit hTNF-α production or activity (such as cyclohexane-ylidene derivatives as described in PCT Publication No. WO 93119751). Furthermore, TNF-α binding molecules of the invention may be used in combination with one or more of the foregoing therapeutic agents. Such combination therapies may advantageously utilize lower dosages of the administered therapeutic agents, thus avoiding possible toxicities or complications associated with the various monotherapies.

Non-limiting examples of therapeutic agents for rheumatoid arthritis with which the TNF-α binding molecules of the invention can be combined include, but are not limited to the following: non-steroidal anti-inflammatory drug(s) (NSAIDs); cytokine suppressive anti-inflammatory drug(s) (CSAIDs); CDP-571/BAY-10-3356 (humanized anti-TNF-α antibody; Celltech/Bayer); cA2 (chimeric anti-TNF-α antibody; Centocor); 75 kDa TNFR-IgG (75 kDa TNF receptor-IgG fusion protein; Immunex; see e.g., Arthritis & Rheumatism (1994) Vol. 37. S295; J. Invest Med. (1996) Vol. 44 235A); 55 kDa TNFR-IgG (55 kDa TNF receptor-IgG fusion protein; Hoffmann-LaRoche); IDEC-CE9.1/SB 210396 (non-depleting primatized anti-CD4 antibody; IDEC/SmithKline; see e.g., Arthritis & Rheumatism (1995) Vol. 38, S185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2R.alpha; Protein Design Labs/Roche); IL-4 (anti-inflammatory cytokine; DNAX/Schering); IL-10 (SCH 52000; recombinant IL-10, anti-inflammatory cytokine; DNAX/Schering); IL-10 and/or IL-4 agonists (e.g., agonist antibodies); IL-1 RA (IL-1 receptor antagonist; Synergen/Amgen); TNF-bp/s-TNFR (soluble TNF binding protein; see e.g., Arthritis & Rheumatism (1996) Vol. 39 No. 9 (supplement), S284; Heart and Circulatory Physiology (1995) Vol. 268, pp. 3742); R973401 (phosphodiesterase Type IV inhibitor; see e.g., Arthritis & Rheumatism (1996) Vol. 39. No. 9 (supplement), S282); MK-966 (COX-2 Inhibitor; see e.g., Arthritis & Rheumatism (1996) Vol. 3, No. 9 (supplement), S81); Iloprost (see e.g., Arthritis & Rheumatism (1996) Vol. 39. No. 9 (supplement), S82); methotrexate: thalidomide (see e.g., Arthritis & Rheumatism (1996) Vol. 9, No. 9 (supplement), S282) and thalidomide-related drugs (e.g., Celgen); leflunomide (anti-inflammatory and cytokine inhibitor; see e.g., Arthritis & Rheumatism (1996) Vol. 39 No. 9 (supplement), S131; Inflammation Research (1996) Vol. 4, pp. 103–107); tranexamic acid (inhibitor of plasminogen activation; see e.g., Arthritis & Rheumatism (1996) Vol. 39, No. 9 (supplement), S284); T614 (cytokine inhibitor; see e.g., Arthritis & Rheumatism (1996) Vol. 39 No. 9 (supplement), S282); prostaglandin E1 (see e.g., Arthritis & Rheumatism (1996) Vol. 39, No. 9 (supplement), S282); Tenidap (non-steroidal anti-inflammatory drug; see e.g., Arthritis & Rheumatism (1996) Vol. 39 No. 9 (supplement), S280); Naproxen (non-steroidal anti-inflammatory drug; see e.g., Neuro Report (1996) Vol. 7, pp. 1209–1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Arthritis & Rheumatism (1996) Vol. 9, No. 9 (supplement), S281); Azathioprine (see e.g., Arthritis & Rheumatism (1996) Vol. 39 No. 9 (supplement), S281); ICE inhibitor (inhibitor of the enzyme interleukin-1 beta converting enzyme); zap-70 and/or Ick inhibitor (inhibitor of the tyrosine kinase zap-70 or Ick); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39. No. 9 (supplement), S120); gold; penicillamine; chloroquine; hydroxychloroquine; chlorambucil; cyclophosphamide; cyclosporine; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone. orgotein; glycosaninoglycan polysulphate; minocycline; anti-IL-2R antibodies; marine and botanical lipids (fish and plant seed fatty acids; see e.g., DeLuca et al. (1995) Rheum. Dis. Clin. North Am. 21:759–777); auranofm; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); azaribine, and the D2E7 antibody (See, U.S. Pat. No. 6,258,562, herein incorporated by reference).

Non-limiting examples of therapeutic agents for inflammatory bowel disease with which the TNF-α binding molecules of the invention can be combined include, but are not limited to, the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1beta monoclonal antibodies; anti-IL-6 monoclonal antibodies; growth factors; elastase inhibitors; pyridinyl-imidazole compounds; CDP-571/BAY-10-3356 (humanized anti-TNF-α antibody; Celitech/Bayer); cA2 (chimeric anti-TNF-α antibody; Centocor); 75 kDa TNFR-IgG (75 kDa TNF receptor-IgG fusion protein;

Immunex; see e.g., Arthritis & Rheumatism (1994) Vol. 7, S295; J. Invest. Med. (1996) Vol. 44 235A); 55 kDa TNFR-IgG (55 kDa TNF receptor-IgG fusion protein; Hoffmann-LaRoche); interleukin-10 (SCH 52000; Schering Plough); IL-4 (anti-inflammatory cytokine; DNAX/Schering); IL-10 and/or IL4 agonists (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

Non-limiting examples of therapeutic agents for multiple sclerosis with which the TNF-α binding molecules of the invention can be combined include, but are not limited to, the following: corticosteroids; prednisolone; methylprednisolone; azathioprine; cyclophosphamide; cyclosporine; methotrexate; 4-aminopyridine; tizanidine; interferon-beta1a (Avonex.TM.; Biogen); interferon-beta1b (Betaseron.TM.; Chiron/Berlex); Copolymer 1 (Cop1; Copaxone.TM.; Teva Pharmaceutical Industries, Inc.); hyperbaric oxygen; intravenous immunoglobulin; clabribine; CDP-571/BAY-10-3356 (humanized anti-TNF-α antibody; Celltech/Bayer); cA2 (chimeric anti-TNF-α antibody; Centocor); 75 kDa TNFR-IgG (75 kDa TNF receptor-IgG fusion protein; Immunex; see e.g., Arthritis & Rheumatism (1994) Vol. 37, S295; J. Invest. Med. (1996) Vol. 44, 235A); 55 kDa TNFR-IgG (55 kDa TNF receptor-IgG fusion protein; Hoffmann-LaRoche); IL-10; IL-4 (anti-inflammatory cytokine; DNAX/Schering); and IL-10 and/or IL-4 agonists (e.g., agonist antibodies).

Non-limiting examples of therapeutic agents for sepsis with which the TNF-α binding molecules of the invention can be combined include, but are not limited to, the following: hypertonic saline solutions; antibiotics; intravenous gamma globulin; continuous hemofiltration; carbapenems (e.g., meropenem); antagonists of cytokines such as TNF-α, IL-6 and/or IL-8; CDP-571/BAY-10-3356 (humanized anti-TNF-α antibody; Celltech/Bayer); cA2 (chimeric anti-TNF-α antibody; Centocor); 75 kDa TNFR-IgG (75 kDa TNF receptor-IgG fusion protein; Immunex; see e.g., Arthritis & Rheumatism (1994) Vol. 37, S295; J. Invest. Med. (1996) Vol. 44, 235A); 55 kDa TNFR-IgG (55 kDa TNF receptor-IgG fusion protein; Hoffmann-LaRoche); Cytokine Regulating Agents (CRAs) HP228 and HP466 (Houghten Pharmaceuticals, Inc.); SK&F 107647 (low molecular peptide; SmithKline Beecham); tetravalent guanylhydrazone CNI-1493 (Picower Institute); Tissue Factor Pathway Inhibitor (TFPI; Chiron); PHP (chemically modified hemoglobin; APEX Bioscience); iron chelators and chelates, including diethylenetriamine pentaacetic acid-iron (III) complex (DTPA iron (III); Molichem Medicines); lisofylline (synthetic small molecule methylxanthine; Cell Therapeutics, Inc.); PGG-Glucan (aqueous soluble β-1,3 glucan; Alpha-Beta Technology); apolipoprotein A-I reconstituted with lipids; chiral hydroxamic acids (synthetic antibacterials that inhibit lipid A biosynthesis); anti-endotoxin antibodies; E5531 (synthetic lipid A antagonist; Eisai America, Inc.); rBPI21 (recombinant N-terminal fragment of human Bactericidal/Permeability-Increasing Protein); the D2E7 antibody, and Synthetic Anti-Endotoxin Peptides (SAEP; Bios Ynth Research Laboratories).

Non-limiting examples of therapeutic agents for adult respiratory distress syndrome (ARDS) with which the TNF-α binding molecules of the invention can be combined include the following: anti-IL-8 antibodies; surfactant replacement therapy; CDP-571/BAY-10-3356 (humanized anti-TNF-α antibody; Celltech/Bayer); cA2 (chimeric anti-TNF-α antibody; Centocor); 75 kDa TNFR-IgG (75 kDa TNF receptor-IgG fusion protein; Immunex; see e.g., Arthritis & Rheumatism (1994) Vol. 3.7 S295; J. Invest. Med. (1996) Vol. 44, 235A); and 55 kDa TNFR-IgG (55 kDa TNF receptor-IgG fusion protein; Hoffmann-LaRoche).

The pharmaceutical compositions of the invention may include a "therapeutically effective amount" or a "prophylactically effective amount" of an antibody or antibody fragment of the invention. A "therapeutically effective amount" refers to an amount effective, at dosages and for periods of time necessary, to achieve the desired therapeutic result. A therapeutically effective amount of the antibody or antibody fragment may vary according to factors such as the disease state, age, sex, and weight of the individual, and the ability of the antibody or antibody fragment to elicit a desired response in the individual. A therapeutically effective amount is also one in which any toxic or detrimental effects of the antibody or antibody fragment are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

IV. Additional TNF-α Binding Molecule Uses

The present invention also provides TNF-α binding molecules (e.g., anti-TNF-α peptides and antibodies) detectably labeled, as described below, for use in diagnostic methods for detecting TNF-α in patients known to be or suspected of having a TNF-α-mediated disease.

TNF-α binding molecules of the present invention, such as anti-TNF-α peptides and/or antibodies are useful for immunoassays which detect or quantify TNF-α in a sample. An immunoassay for TNF-α typically comprises incubating a biological sample in the presence of a detectably labeled high affinity anti-TNF-α peptide and/or antibody of the present invention capable of selectively binding to TNF-α, and detecting the labeled peptide or antibody which is bound in a sample. Various clinical assay procedures are well known in the art, e.g., as described in Immunoassays for the 80's, A. Voller et al., eds., University Park, 1981.

Thus, an anti-TNF peptide or antibody, can be captured on nitrocellulose, or on any other solid support which is capable of immobilizing soluble proteins. A TNF-α-containing sample is then added to the support which is subsequently washed with suitable buffers to remove unbound proteins. A second, detectably labeled, TNF-α specific peptide or antibody is added to the solid phase support that can then be washed with the buffer a second time to remove unbound detectably labeled peptide or antibody. The amount of bound label on the solid support can then be detected by known methods.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule retains its ability to bind to TNF-α. Thus, the support configuration can be spherical, as in a bead, or cylindrical, as in the inside surface of a test tube, or the external surface of a rod. Alternatively, the surface can be flat such as a sheet, culture dish, test strip, microtiter plates, etc. Preferred supports include polystyrene beads. Those skilled in the art will know many other suitable carriers for binding antibody, peptide or antigen, or can ascertain the same by routine experimentation. Well known methods can be used to determine the binding activity of a given lot of anti-TNF-α peptide and/or antibody. Those skilled in the art can determine operative and optimal assay conditions by routine experimentation.

Detectably labeling a TNF-α binding molecule, such as a TNF-specific peptide and/or antibody, can be accomplished by coupling to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the TNF-α binding molecules of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the TNF-α binding molecules, it is possible to detect TNF-α through the use of a radioimmunoassay (RIA) (see, for example, Work, et al., (1978) Laboratory Techniques and Biochemistry in Molecular Biology, North Holland Publishing Company, N.Y.). The radioactive isotope can be detected by such means as the use of a gamma counter or a scintillation counter or by autoradiography.

It is also possible to label the TNF-α binding molecules with a fluorescent compound. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The TNF-α binding molecules can also be detectably labeled using fluorescence-emitting metals such as $^{125}$Eu, or others of the lanthamide series. These metals can be attached to the TNF-α binding molecule using such metal chelating groups as diethylenetriaminepentaacetic acid (DTPA) or ethylenediamine-tetraacetic acid (EDTA).

The TNF-α binding molecules also can be detectably labeled by coupling to a chemiluminescent compound. The presence of the chemiluminescently labeled molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the TNF-α binding molecules of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the TNF-α binding molecules can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate to similarly prepared standards.

In some embodiments of the present invention, the TNF-α which is detected by the above assays can be present in a biological sample. Any sample containing TNF-α can be used. Preferably, the sample is a biological fluid such as, for example, blood, serum, lymph, urine, cerebrospinal fluid, amniotic fluid, synovial fluid, a tissue extract or homogenate, and the like. However, the invention is not limited to assays using only these samples, as it is possible for one of ordinary skill in the art to determine suitable conditions which allow the use of other samples.

In situ detection can be accomplished by removing a histological specimen from a patient, and providing the combination of labeled TNF-α binding molecules of the present invention to such a specimen. The TNF-α binding molecule is preferably provided by applying or by overlaying the labeled TNF-α binding molecule to a biological sample. Through the use of such a procedure, it is possible to determine not only the presence of TNF-α but also the distribution of TNF-α in the examined tissue. Using the present invention, those of ordinary skill will readily perceive that any of a wide variety of histological methods (such as staining procedures) can be modified in order to achieve such in situ detection.

The TNF-α binding molecules of the present invention can be adapted for utilization in an immunometric assay, also known as a "two-site" or "sandwich" assay. In a typical immunometric assay, a quantity of unlabeled TNF-α binding molecule (such as an anti-TNF-α antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, and preferred, immunometric assays include "forward" assays in which the TNF-α binding molecule (e.g. antibody) bound to the solid phase is first contacted with the sample being tested to extract the TNF-α from the sample by formation of a binary solid phase antibody-TNF-α complex. After a suitable incubation period, the solid support is washed to remove the residue of the fluid sample, including unreacted TNF-α, if any, and then contacted with the solution containing a known quantity of labeled antibody (which functions as a "reporter molecule"). After a second incubation period to permit the labeled antibody to complex with the TNF-α bound to the solid support through the unlabeled antibody, the solid support is washed a second time to remove the unreacted labeled antibody. This type of forward sandwich assay can be a simple "yes/no" assay to determine whether TNF-α is present or can be made quantitative by comparing the measure of labeled antibody with that obtained for a standard sample containing known quantities of TNF-α. Such "two-site" or "sandwich" assays are described by Wide (Radioimmune Assay Method, Kirkham, ed., Livingstone, Edinburgh, 1970, pp. 199–206).

Other types of "sandwich" assays, which can also be useful with TNF-α, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay. In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

In some embodiments, the TNF-α binding molecules of this invention, attached to a solid support, can be used to remove TNF-α from fluids or tissue or cell extracts. In a preferred embodiment, they are used to remove TNF-α from blood or blood plasma products. In another preferred embodiment, the TNF-α binding molecules are advantageously used in extracorporeal immunoadsorbent devices, which are known in the art (see, for example, Seminars in Hematology, 26 (2 Suppl. 1)(1989)). Patient blood or other body fluid is exposed to the attached TNF-α binding molecule, resulting in partial or complete removal of circulating TNF-α (free or in immune complexes), following which the fluid is returned to the body. This immunoadsorption can be implemented in a continuous flow arrangement, with or without interposing a cell centrifugation step. See, for example, Terman, et al., (1976) J. Immunol. 117:1971–1975.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); nM (nanomolar); pM (picomolar); mg (milligrams); μg (micrograms); pg (picograms); ml (milliliters); μl (microliters); ° C. (degrees Celsius); OD (optical density); nm (nanometer); BSA (bovine serum albumin); and PBS (phosphate-buffered saline solution).

EXAMPLE 1

Construction and Screening of Anti-TNF-α Fab Fragments with Synthetic CDRs and Human Frameworks This example describes the construction of anti-TNF-α Fab fragments with fully human framework regions and synthetic CDRs. The nucleic acid sequences encoding the hu1 CDRs and framework regions are shown in SEQ ID NOs: 2 and 4, respectively. The six hu1 CDRs employed were as follows: CDRL1 (SEQ ID NO: 10); CDRL2 (SEQ ID NO: 20); CDRL3 (SEQ ID NO: 34); CDRH1 (SEQ ID NO: 36); CDRH2 (SEQ ID NO: 44); and CDRH3 (SEQ ID NO: 54).

In order to identify mutations that improve the binding properties of hu1, libraries of synthetic CDRs were inserted into a deletion template as described below. Standard mutagenesis techniques (Kunkel, T. A., (1985) Proc. Natl. Acad. Sci. U.S.A, 82: 488–492, herein incorporated by reference) were employed to individually replace each hu1 CDR with a pool of mutagenic oligonucleotides. In this example, the CDRs include residues that encompass both the Kabat and Chothia definitions (e.g., residues 26–35 for CDRH1). The length of CDRH2 made it necessary to construct two separate libraries to cover the entire region.

Mutagenic oligonucleotides were annealed to a uridinylated phage template in which the corresponding hu1 CDR was deleted. This template was composed of the hu1 light chain variable region sequence (SEQ ID NO: 2, with the appropriate hu1 CDR deleted) and the human CL sequence shown in SEQ ID NO: 85 as well as the hu1 heavy chain variable region sequence (SEQ ID NO: 4, with the appropriate hu1 CDR deleted) and the human CH1 sequence shown in SEQ ID NO: 86.

Annealing was accomplished by incubating the reaction at 75° C. for 5 minutes followed by slow cooling to 20° C. over the course of 45 minutes. The annealed samples were placed on ice and T4 DNA polymerase and T4 DNA ligase were added to generate double stranded DNA and the reaction was incubated for 5 minutes at 4° C. followed by 90 minutes at 37° C. The reaction was phenol extracted, ethanol precipitated and the DNA was electroporated into DH10B cells. XL1 Blue cells were added to the reaction to allow phage amplification before the libraries were plated. Phage stocks were prepared by the addition of 8 ml of growth medium to the plates followed by incubation at 4° C. for a minimum of 4 hours. The phage-containing medium was harvested and clarified by centrifugation and sodium azide (0.02%) was added as a preservative.

Initial screening of the anti-TNF-α Fab libraries was done by a plaque lift as described in Watkins, J. D. et al., (1998) Anal. Biochem., 256: 169–177, herein incorporated by reference. Briefly, nitrocellulose filters were coated with goat anti-human kappa antibodies, blocked with 1% BSA and placed on plates containing plaques generated from the phage libraries for 16 hours at 22° C. Filters were then rinsed in PBS and incubated with varying concentrations of biotinylated human TNF-α for varying lengths of time. Filters were washed in PBS containing 0.1% Tween 20, incubated with NeutrAvidin alkaline phosphatase conjugate for 2–60 minutes and washed in the same buffer. Differences in signal intensity revealed by the addition of standard colorimetric subtrates for alkaline phosphatase were used to identify variants with improved binding properties. This screening procedure resulted in the identification of several Fab fragments that were further characterized as follows:

Positive plaques were picked with a Pasteur pipet and phages were eluted for 1 hour at 37° C. in 100 μl, of 10 mM Tris HCl, pH 7.4 and 100 mM NaCl. High titer stocks were then obtained by standard amplification techniques. XL1 Blue cells were grown to an $OD_{600}$ of 1 and IPTG was added to a final concentration of 1 mM. Following infection of 15 ml of bacterial culture with 10 μl of high titer phage stock, cells were incubated at 37° C. for an hour and at 22° C. for 16 hours. Bacteria were harvested and washed with 30 mM Tris HCl, pH 8 and 150 mM NaCl. The pellet was resuspended in 640 μl of 30 mM Tris HCl, pH 8, 2 mM EDTA and 20% sucrose and incubated at 4° C. for 15 minutes. Lysed cells were pelleted and the supernatant containing the periplasmic content and Fab fragments was assayed in an ELISA format to determine approximate off-rates. COSTAR #3366 microtiter plates were coated with 1 μg/ml of hTNF-α in carbonate buffer for 16 hours at 4° C. The plates were washed 3 times with PBS containing 0.1% Tween 20 and blocked with 1% BSA for 1 hour at 22° C. Fab fragments released from the periplasmic space were serially diluted in PBS containing 0.05% Tween 20 and added to the plates for 1 hour at 22° C. The plates were washed and incubated with goat anti-human kappa antibodies conjugated to alkaline phosphatase in PBS containing 0.05% Tween 20 for 1 hour at 22° C. The plates were then washed with PBS containing 0.1% Tween 20 and developed with standard colorimetric substrates for alkaline phosphatase (see, e.g., Watkins, J. D. et al., (1997) Anal. Biochem., 253: 37–45, herein incorporated by reference).

ELISA assays were also used to determine approximate on-rates. COSTAR #3366 microtiter plates were coated with 2 μg/ml of goat anti-human kappa antibodies in carbonate buffer for 16 hours at 4° C. Fab fragments released from the periplasmic space were serially diluted in PBS containing 0.05% Tween 20 and added to wells and incubated for 1 hour at 22° C. The plates were washed 3 times with PBS containing 0.1% Tween 20 and incubated with 5 nM biotinylated hTNF-α for 2 minutes at 22° C. The plates were washed once and NeutrAvidin alkaline phosphatase conjugate was added for 2 minutes at 22° C. The plates were washed and developed as above. The initial filter lift screening procedure and the subsequent characterization of the positive variants in ELISA assays revealed single amino acid changes in the individual CDRs of several Fab fragments that result in an increase in affinity for TNF-α in the context of fully human frameworks. These amino acid changes are listed in Table 1, Table 2 and Table 3.

A library where the single beneficial mutations were combined to assess their additivity was constructed using the procedure described above. This library was screened using the three assays described in the previous sections and a panel of combinatorial variants with improved binding properties is shown in FIG. 7. The names of the particular clones identified are provided in Table 4 below, along with the beneficial mutations (defined by the original residue in hu1 followed by the new residue in the particular clone).

TABLE 4

| Clone | Light chain mutations | Heavy chain mutations |
|---|---|---|
| 2C6K | S31L, S54Y | T28K, E61R |
| 2C6P | S31L, S54Y | T28P, E61R |
| 2E7K | S31L, M55R | T28K, I53M, E61R |
| 2E7P | S31L, M55R | T28P, I53M, E61R |
| A9K | S31M, M55K | T28K, I53M, E61R |
| A9P | S31M, M55K | T28P, I53M, E61R |
| A10K | S31Y, M55R | T28K, I53M |
| A10P | S31Y, M55R | T28P, I53M |

Next, binding kinetics of three of the Fab fragments described in Table 4 were determined in a kinetic exclusion assay. Affinity measurements were performed on a KinExA™3000 instrument (Sapidyne Instruments, Inc., Boise, Id.) using Fab fragments (A10K, A9K, and A10P) released from the periplasmic space whose concentration was determined by a quantitative ELISA. Briefly, antigen and antibody fragment were allowed to react in solution and the fraction of unbound reagent was determined by capture and measured on a bead support. Binding kinetics can be determined or calculated from the amount of unbound reagent. For instance, after interaction between TNF-α and a Fab fragment has occurred in solution, binding of the unreacted, free Fab fragment to TNF-α coated beads can be measured on the instrument by detection with a labeled secondary antibody to the Fab fragment (e.g., a goat anti-IgG (heavy and light)). To measure $K_d$, individual tubes containing a constant concentration of Fab fragment with decreasing concentrations of human TNF-α were incubated for 20 hours at 20° C. in PBS supplemented with 0. % BSA. A total of 13 tubes were used for each $K_d$ determination. For A10K and A10P, the Fab concentration was 10 pM with the human TNF-α concentration beginning at 160 pM and then serially diluted to 0.078 pM with the final tube containing no human TNF-α. A9K incubation was set in a similar manner, with the Fab at a constant concentration of 20 pM and human TNF-α serially diluted beginning at 500 pM with a final concentration of 0.24 pM. After the incubation, the amount of unbound Fab in the equilibrated samples was determined on the KinExA™3000 instrument according to the manufacturer's instructions. $K_d$ values were determined by the instrument software. The results are provided in Table 5.

To measure $k_{on}$, individual Fab fragments at a concentration of 40 pM were mixed with 400 pM of hTNF-α. A series of measurements were taken over a time course. The resulting data was used to calculate the $k_{on}$ with the instrument software. $k_{off}$ was calculated by using the formula $K_d = k_{off}/k_{on}$. The results are provided in Table 5.

TABLE 5

| Clone | $K_d$ (pM) | $k_{on}$ ($M^{-1}sec^{-1}$) | $k_{off}$ ($sec^{-1}$) |
|---|---|---|---|
| A10K | 3.5–7.2 | 3.92–7.51 × $10^6$ | 1.96–3.76 × $10^{-5}$ |
| A9K | 2.4 | 2.6 × $10^6$ | 6.2 × $10^{-6}$ |
| A10P | 2.0 | 4.1 × $10^6$ | 8.2 × $10^{-6}$ |

EXAMPLE 2

Figure 8:
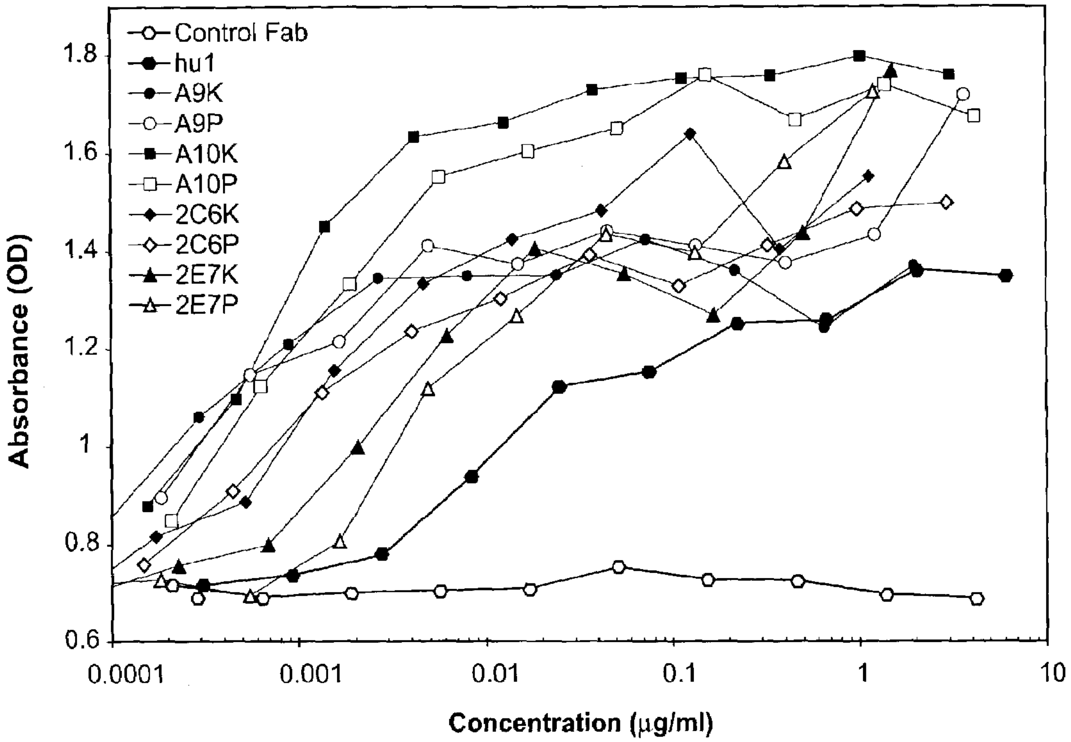
FIG. 8 shows the results of an L929 cell protection assay described in Example 2.

Characterization of Anti-TNF-α Binding Molecules with Improved Binding Properties This example describes various in vitro testing procedures used to identify particular characteristics of the eight anti-TNF-α binding molecules from Example 1. First, the ability of these Fab fragments to prevent TNF-α-mediated cell death was assessed by evaluating their protective effects on L929 mouse fibroblasts. Specifically, L929 mouse fibroblast cells were distributed in individual wells in a 96-well plate at a density of 20,000 cells per well and maintained according to ATCC recommendations. After overnight incubation, Fab fragments released from the periplasmic space were serially diluted in culture medium, sterile filtered and 50 μl were added to the wells along with actinomycin D to a final concentration of 1 μg/ml. Immediately thereafter, hTNF-α was added to a final concentration of 80 pg/ml and the plates were placed in a humidified incubator at 37° C. in a 5% $CO_2$ atmosphere. After overnight incubation, the protective effects of the various Fab fragments were assessed by monitoring cell survival using the Cell Titer 96® AQueous One solution reagent (Promega, Madison Wis.) according to the manufacturer's instructions. The optical density of individual wells was measured at 490 nm and the results are shown in FIG. 8. At the TNF-α concentration used, approximately 90% of L929 cells died after overnight incubation and the addition of an unrelated control Fab fragment did not confer any protection. In contrast, each of the eight anti-TNF-α Fab fragments described in Table 4 was able to prevent cell death. Among these TNF-α binding molecules, A10K and A10P were able to protect cells at the lowest concentration, reflecting improved binding properties for TNF-α. The effective concentration ($EC_{50}$) was determined using the curve fitting function and $EC_{50}$ derivation capabilities of the SigmaPlot® software (SPSS Science, Chicago, Ill.). In the experiment shown in FIG. 8, the $EC_{50}$ of the A10K Fab fragment was estimated at approximately 25 pM.

In order to further evaluate clones in Table 4 (e.g. A10K) as full IgG molecules, instead of Fab fragments, the following procedure may be employed. First, the light chain variable region (VL) and the heavy chain variable region (VH) can be transferred from the A10K Fab expressing phage into, for instance, an expression vector containing both the heavy and light chain constant regions. Alternatively, the variable regions can be cloned into two separate expression vectors, each vector eventually expressing only one of the two chains. The VL region can be amplified by PCR using the following primers: VL 5' primer: TGGCTCCCAGGTGCCAAATGTGAAATTGTGCTGACTCAG (SEQ ID NO: 87); VL 5' biotinylated primer: Biotin-TGGCTCCCAGGTGCCAAATGT (SEQ ID NO: 88); and VL 3' primer: GACAGATGGTGCAGCCACAGT (SEQ ID NO: 89). Similarly, the VH region can be amplified using the following primers (VH 5' primer: CTCTCCACAGGTGTCCACTCCCAGGTCCAACTGCAGGTC (SEQ ID NO: 90); VH 5' biotinylated primer: Biotin-CTCTCCACAGGTGTCCACTCC (SEQ ID NO: 91); and VH 3' primer: GAAGACCGATGGGCCCTTGGT (SEQ ID NO: 92). After PCR amplification, the biotinylated DNA strand is removed and the non-biotinylated strand is annealed to single stranded uridinylated template prepared from the expression vector at an annealing ratio of 20:1, followed by synthesis with T4 DNA polymerase in presence of T4 DNA ligase. In DH10B cells, the uridinylated template is lost, yielding a double stranded plasmid with, for instance, the A10K IgG.

Next, mammalian cells (e.g., CHO-K1 cells) are transfected with the expression vector(s) and a pool of stable integrants can be selected by culturing the transfected cells in an appropriate medium and under appropriate selection. Upon confirmation of IgG expression by ELISA, the pool can be expanded, for instance in roller bottles, and maintained in selection. The medium is usually changed once every other day and the conditioned medium containing the A10K IgG is used for IgG purification. This same procedure may be employed to generate a hu1 IgG or any other IgG molecule.

Figure 9:
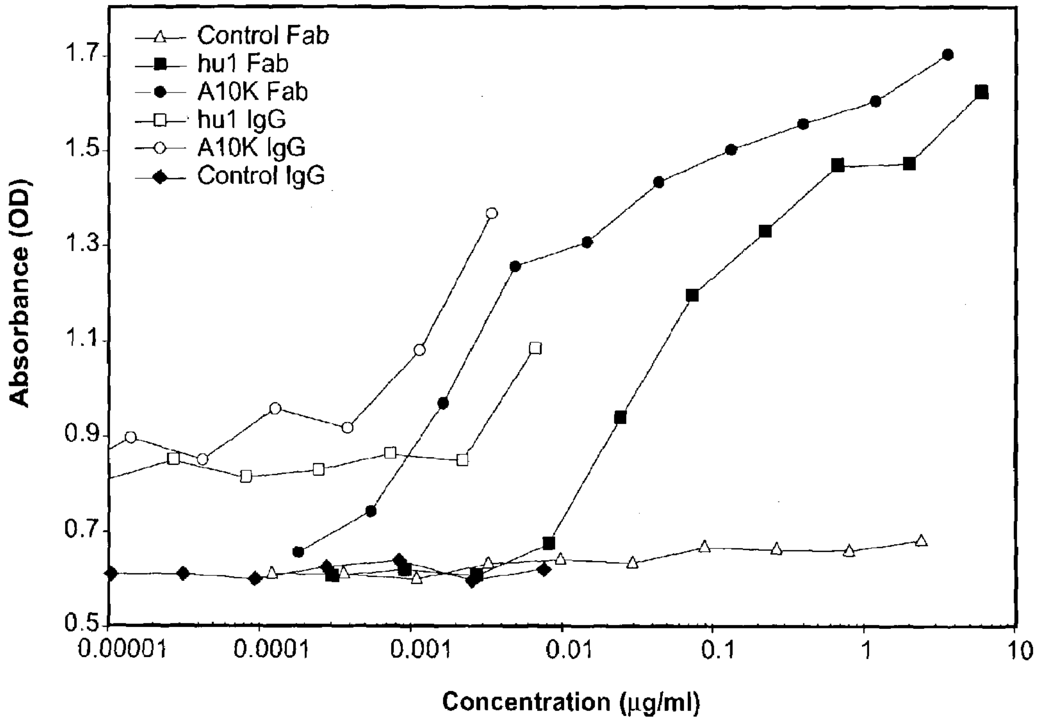
FIG. 9 shows the results of an L929 cell protection assay described in Example 2.

The L929 cell protection assay was used to characterize A10K and hu1 both as Fab fragments and as intact IgG molecules, along with a control Fab and a control IgG. The assay was performed as described in the previous section. As shown in FIG. 9, both TNF-α binding molecules, either as Fab fragments or as intact IgGs, were able to protect cells from the detrimental effects of TNF-α. However, the concentration of A10K necessary to achieve identical protection is significantly lower than that of hu1, showing that the improvements in binding properties achieved by protein engineering translate into lower effective doses on cells. In this experiment, the $EC_{50}$ of the A10K Fab fragment was estimated at approximately 67 pM.

Figure 10:
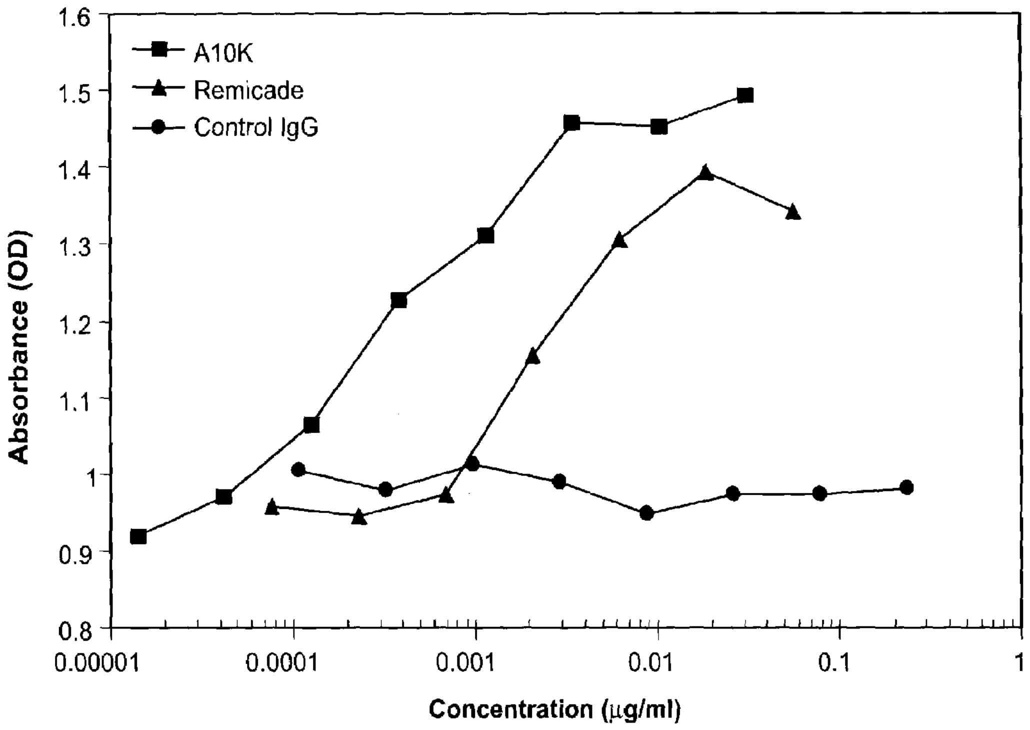
FIG. 10 shows the results of an L929 cell protection assay described in Example 2.

FIG. 10 shows a direct comparison between A10K and REMICADE (Oncology Supply, Dothan, Ala.), a standard of care in rheumatoid arthritis and Crohn's disease. Similarly, both A10K and Remicade are able to fully protect L929 fibroblasts but A10K is able to achieve identical protection at drastically lower concentrations, demonstrating that A10K is a more potent molecule and is more effective at neutralizing TNF-α. The $EC_{50}$ of the A10K IgG molecule was estimated at approximately 2.7 pM.

EXAMPLE 3

In Vivo Examples with A10K

This example describes two in vivo assays with the A10K intact IgG. In particular, this example describes the in vivo TNF-α neutralizing effects of A10K in mice, as well as the protective effects of A10K on TNF-α mediated polyarthritis in mice.

Figure 11:
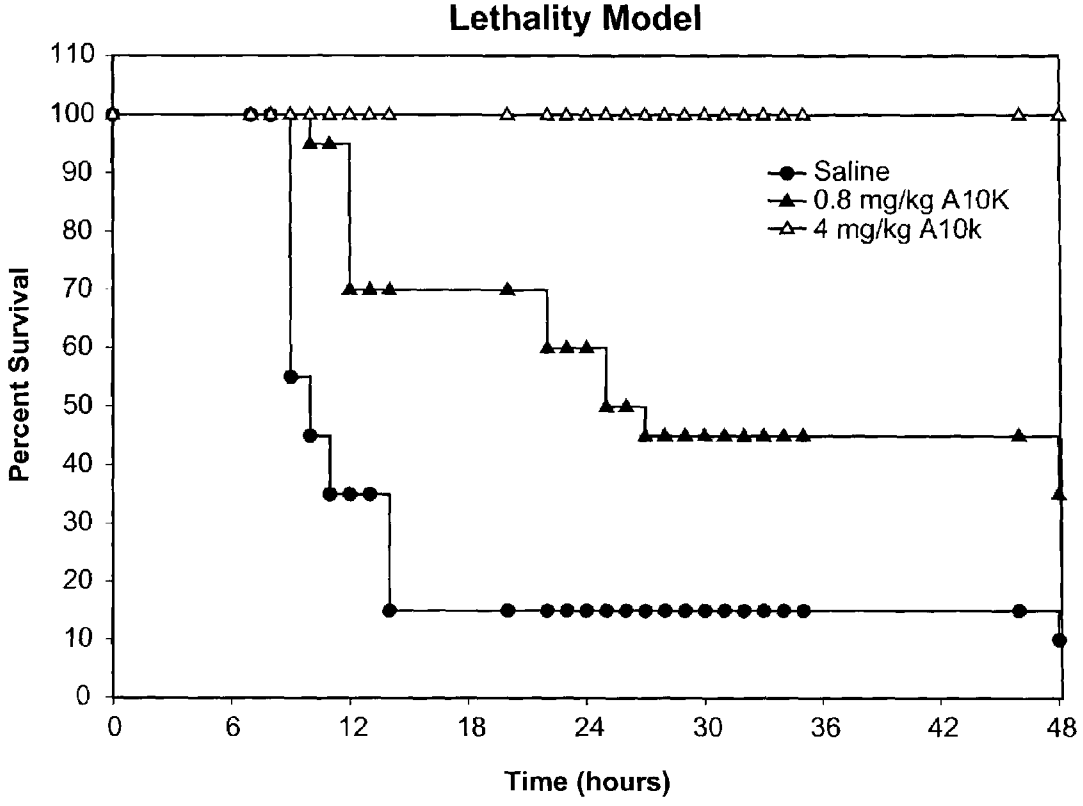
FIG. 11 shows the results of an in vivo TNF-α neutralizing assay described in Example 3.

The TNF-α neutralizing ability of A10K in vivo was evaluated as follows. Female C3H/HeN mice (~9 weeks of age) were injected intraperitoneally with recombinant human TNF-α (5 μg/mouse) in combination with the sensitizing agent galactosamine (18 mg/mouse). In untreated mice, these conditions result in approximately 90 percent mortality within 48 hours. The neutralizing effect of A10K was evaluated by injecting mice with 0.8 and 4 mg/kg, intravenously, 24 hours prior to hTNF-α challenge. A10K demonstrated a dose-dependent inhibition of mortality, with complete protection being observed at the higher dose investigated. These results are presented in FIG. 11.

Figure 12:
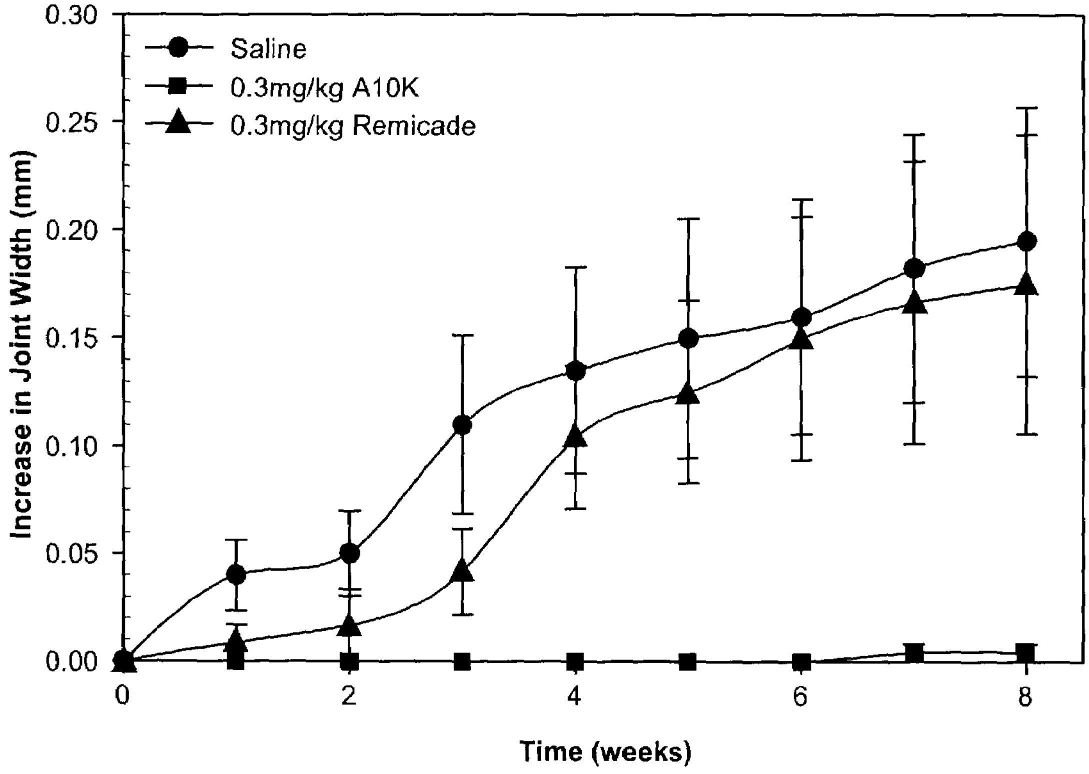
FIG. 12 shows the effect of a TNF-α binding molecule in reducing progression of TNF-α mediated polyarthritis in mice, as described in Example 3.

The effect of A10K on TNF-α mediated polyarthritis was evaluated as follows. C57BL/6NTac-TgN (TNF) mice transgenic for human hTNF-α develop severe chronic arthritis by approximately 20 weeks of age (Keffer, J. et al., (1991) EMBO J., 10:4025–4031, herein incorporated by reference). A dose escalation study was performed on mice exhibiting very early stage joint swelling (9 weeks of age) to determine the effects of A10K on disease progression. Hind joint width was determined and animals were randomized into groups and balanced for initial joint size. Animals were then injected intraperitoneally with 0.1, 0.3 or 1 mg/kg of A10K or control REMICADE (Oncology Supply, Dothan, Ala. Joint swelling was monitored weekly by measuring the increase in joint width (joint width at $t_x$-joint width at $t_o$). A10K exhibited a dose-dependent inhibition in the progression of polyarthritis and was more effective than REMICADE (Oncology Supply, Dothan, Ala.) at similar doses. These results are presented in FIG. 12.

EXAMPLE 4

Use of TNF-α Binding Molecules to Treat a TNF-α Mediated Disease

This example describes the use of TNF-α binding molecules for the therapeutic and prophylactic treatment of a TNF-α mediated disease in a human patient (e.g., with juvenile and adult rheumatoid arthritis, psoriatic arthritis, Crohn's disease, inflammatory bowel disease, ulcerative colitis, psoriasis, ankylosing spondylitis, Wegener's granulomatosis and sepsis). For example, a patient with a TNF-α mediated disease may be administered a single dose of an anti-TNF-α binding molecule, such as 2C6K, 2C6P, 2E7K, 2E7P, A9K, A9A10K, A10P, or hu1, intravenously at 1–15 milligrams per kilogram of patient body weight. This patient, however, may also be given multiple doses over time (e.g. 3 mg/kg over multiple days or weeks). Response to therapy may be monitored to determine the need for increased or reduced dosage and the need for repeat treatment. Additional guidance on response to therapy and dosage schedules is found in U.S. Pat. No. 5,698,195, herein incorporated by reference. The patient may also be administered an immunosuppressant, such as methotrexate, in combination with the TNF-α binding molecule.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

---

We claim:

1. A TNF-α binding molecule selected from the group consisting of:

(i) an antibody or antibody fragment comprising a light chain variable region comprising a polypeptide with SEQ ID NO: 1, and further comprising a heavy chain variable region comprising a polypeptide with SEQ ID NO: 3;

(ii) an antibody or antibody fragment comprising a light chain variable region comprising a polypeptide with SEQ ID NO: 1 with S31L and S54Y substitutions, and further comprising a heavy chain variable region comprising a polypeptide with SEQ ID NO: 3 with T28K and E61R substitutions;

(iii) an antibody or antibody fragment comprising a light chain variable region comprising a polypeptide with SEQ ID NO: 1 with S31L and S54Y substitutions, and further comprising a heavy chain variable region corny rising a polypeptide with SEQ ID NO: 3 with T28P and E61R substitutions, (iv) an antibody or antibody fragment comprising a light chain variable region comprising a polypeptide with SEQ ID NO: 1 with S31L and M55R substitutions, and further comprising a heavy chain variable region a polypeptide with SEQ ID NO: 3 with T28K, I53M and E61R substitutions;

(v) an antibody or antibody fragment comprising a light chain variable region comprising a polypeptide with SEQ ID NO: 1 with S31and M55R substitutions, and further comprising a heavy chain variable region comprising a polypeptide with SEQ ID NO: 3 with T28P, I53M and E61R substitutions;

(vi) an antibody or antibody fragment comprising a light chain variable region comprising a polypeptide with SEQ ID NO: 1 with S31M and M55K substitutes and, and further comprising a heavy chain variable region comprising a polypeptide with SEQ ID NO: 3 with T28K, I53M and E61R substitutions;

(vii) an antibody or antibody fragment comprising a light chain variable region comprising a polypeptide with SEQ ID NO: 1 with S31M and M55K substitutions, and further comprising a heavy chain variable region comprising a polypeptide with SEQ ID NO: 3 with T28P, 153M and E61R substitutions;

(viii) an antibody or antibody fragment comprising a light chain variable region comprising a polypeptide with SEQ ID NO: 1 with S31Y sod M55R substitutions (SEQ ID NO:5), and further comprising a heavy chain variable region comprising a polypeptide with SEQ ID NO: 3 with T28K and I53M substitutions (SEQ ID NO: 7); and (ix) an antibody or antibody fragment comprising a light chain variable region comprising a polypeptide with SEQ ID NO: 1 with S31Y and M55R substitutions and further comprising a heavy chain variable region comprising a polypeptide with SEQ ID NO: 3 with T28P and I53M substitutions.

2. The antibody of claim 1, wherein said antibody has a binding affinity for human TNF-α of about $7.5\times10^{-12}$ M or less.

3. The antibody of claim 1, wherein said antibody has a dissociation rate constant for human TNF-α of about $1.0\times10^{-4}$ $s^{-1}$ or less.

4. The antibody of claim 1, wherein said antibody has an association rate constant for human TNF-α of $3.0\times10^{6}$ $M^{-1}$ $s^{-1}$ or greater.

5. An anti-TNF-α antibody or antibody fragment comprising a light chain variable region comprising a polypeptide with SEQ ID NO: 5 and further comprising a heavy chain variable region comprising a polypeptide with SEQ ID NO: 7.

* * * * *

UNITED STATES PATENT AND TRADEMARK OFFICE

CERTIFICATE OF CORRECTION

PATENT NO. : 7,101,978 B2 Page 1 of 1
APPLICATION NO. : 10/338552
DATED : September 5, 2006
INVENTOR(S) : Jeffry D. Watkins et al.

It is certified that error appears in the above-identified patent and that said Letters Patent is hereby corrected as shown below:

Page 83, Line 39, Under Claim I, (iii), the word “corny rising” should read --comprising--

Signed and Sealed this

Fifth Day of December, 2006

JON W. DUDAS
*Director of the United States Patent and Trademark Office*

SEQUENCE LISTING

```
<160> NUMBER OF SEQ ID NOS: 92

<210> SEQ ID NO 1
<211> LENGTH: 107
<212> TYPE: PRT
<213> ORGANISM: Artificial Sequence
<220> FEATURE:
<223> OTHER INFORMATION: Synthetic

<400> SEQUENCE: 1

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp His Phe
                85                  90                  95

Thr Phe Gly Gln Gly Thr Lys Val Glu Ile Lys
            100                 105


<210> SEQ ID NO 2
<211> LENGTH: 321
<212> TYPE: DNA
<213> ORGANISM: Artificial Sequence
<220> FEATURE:
<223> OTHER INFORMATION: Synthetic

<400> SEQUENCE: 2

gaaattgtgc tgactcagtc tccagacttt cagtctgtga ctccaaaaga gaaagtcacc      60

atcacctgca gggccagtca gttcgttggc tcaagcatcc actggtacca gcagaagcca     120

gatcagtctc caaagctcct catcaagtat gcttctgagt ctatgtctgg ggtcccctcg     180

aggttcagtg gcagtggatc tgggacagat ttcaccctca ccatcaatag cctggaagct     240

gaagatgctg ccacgtatta ctgtcaacaa agtcatagct ggcatttcac gttcggccaa     300

gggaccaagg tggaaatcaa a                                               321


<210> SEQ ID NO 3
<211> LENGTH: 120
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Asn His
20 25 30

Trp Met Asn Trp Val Arg Gln Ala Pro Gly Lys Gly Leu Glu Trp Val
35 40 45

Gly Glu Ile Arg Ser Lys Ser Ile Asn Ser Ala Thr His Tyr Ala Glu
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Asn Tyr Tyr Gly Ser Thr Tyr Asp His Trp Gly Gln
100 105 110

Gly Thr Leu Val Thr Val Ser Ser
115 120

<210> SEQ ID NO 4
<211> LENGTH: 360
<212> TYPE: DNA
<213> ORGANISM: Artificial Sequence
<220> FEATURE:
<223> OTHER INFORMATION: Synthetic

<400> SEQUENCE: 4
gaggtgcagc tggtggagtc tgggggaggc ttggtccagc ctggagggtc cctgagactc 60
tcctgtgcag cctctggatt cactttcagt aaccactgga tgaactgggt ccgccaggct 120
ccagggaagg ggctggagtg ggttggcgaa attagatcaa aatctattaa ttctgcaaca 180
cattatgcgg agtctgtgaa agggagattc accatctcaa gagatgattc aaagaactca 240
ctgtacctgc agatgaacag cctgaaaacc gaggacacgg ccgtgtatta ctgtgctaga 300
aattactacg gtagtaccta cgaccattgg ggccaaggga ccctggtcac cgtctcctca 360

<210> SEQ ID NO 5
<211> LENGTH: 107
<212> TYPE: PRT
<213> ORGANISM: Artificial Sequence
<220> FEATURE:
<223> OTHER INFORMATION: Synthetic

<400> SEQUENCE: 5

Glu Ile Val Leu Thr Gln Ser Pro Asp Phe Gln Ser Val Thr Pro Lys
1 5 10 15

Glu Lys Val Thr Ile Thr Cys Arg Ala Ser Gln Phe Val Gly Tyr Ser
20 25 30

Ile His Trp Tyr Gln Gln Lys Pro Asp Gln Ser Pro Lys Leu Leu Ile
35 40 45

Lys Tyr Ala Ser Glu Ser Arg Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys Gln Gln Ser His Ser Trp His Phe
85 90 95

Thr Phe Gly Gln Gly Thr Lys Val Glu Ile Lys
100 105

<210> SEQ ID NO 6
<211> LENGTH: 321
<212> TYPE: DNA

-continued

<213> ORGANISM: Artificial Sequence
<220> FEATURE:
<223> OTHER INFORMATION: Synthetic

<400> SEQUENCE: 6
gaaattgtgc tgactcagtc tccagacttt cagtctgtga ctccaaaaga gaaagtcacc 60
atcacctgca gggccagtca gttcgttggc tatagcatcc actggtacca gcagaagcca 120
gatcagtctc caaagctcct catcaagtat gcttctgagt ctaggtctgg ggtcccctcg 180
aggttcagtg gcagtggatc tgggacagat ttcaccctca ccatcaatag cctggaagct 240
gaagatgctg ccacgtatta ctgtcaacaa agtcatagct ggcatttcac gttcggccaa 300
gggaccaagg tggaaatcaa a 321

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Phe Ser Asn His
            20                  25                  30

Trp Met Asn Trp Val Arg Gln Ala Pro Gly Lys Gly Leu Glu Trp Val
        35                  40                  45

Gly Glu Ile Arg Ser Lys Ser Met Asn Ser Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asn Tyr Tyr Gly Ser Thr Tyr Asp His Trp Gly Gln
            100                 105                 110

Gly Thr Leu Val Thr Val Ser Ser
        115                 120
```

<210> SEQ ID NO 8
<211> LENGTH: 360
<212> TYPE: DNA
<213> ORGANISM: Artificial Sequence
<220> FEATURE:
<223> OTHER INFORMATION: Synthetic

<400> SEQUENCE: 8
gaggtgcagc tggtggagtc tgggggaggc ttggtccagc ctggagggtc cctgagactc 60
tcctgtgcag cctctggatt ccctttcagt aaccactgga tgaactgggt ccgccaggct 120
ccagggaagg ggctggagtg ggttggcgaa attagatcaa aatctatgaa ttctgcaaca 180
cattatgcgg agtctgtgaa agggagattc accatctcaa gagatgattc aaagaactca 240
ctgtacctgc agatgaacag cctgaaaacc gaggacacgg ccgtgtatta ctgtgctaga 300
aattactacg gtagtaccta cgaccattgg ggccaaggga ccctggtcac cgtctcctca 360

<210> SEQ ID NO 9
<211> LENGTH: 11
<212> TYPE: PRT
<213> ORGANISM: Artificial Sequence -continued
<220> FEATURE:
<223> OTHER INFORMATION: Synthetic

<400> SEQUENCE: 9

Arg Ala Ser Gln Phe Val Gly Ser Ser Ile His
1 5 10

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
agggccagtc agttcgttgg ctcaagcatc cac 33

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Arg Ala Ser Gln Phe Val Gly Leu Ser Ile His
1 5 10

<210> SEQ ID NO 12
<211> LENGTH: 33
<212> TYPE: DNA
<213> ORGANISM: Artificial Sequence
<220> FEATURE:
<223> OTHER INFORMATION: Synthetic

<400> SEQUENCE: 12
agggccagtc agttcgttgg ccttagcatc cac 33

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Arg Ala Ser Gln Phe Val Gly Met Ser Ile His
1 5 10

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
agggccagtc agttcgttgg catgagcatc cac 33

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

-continued

Arg Ala Ser Gln Phe Val Gly Tyr Ser Ile His
1 5 10

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
agggccagtc agttcgttgg ctatagcatc cac 33

<210> SEQ ID NO 17
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 17

Arg Ala Ser Gln Phe Val Gly Xaa Ser Ile His
1 5 10

<210> SEQ ID NO 18
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(24)
<223> OTHER INFORMATION: n is a, c, g, or t

<400> SEQUENCE: 18
agggccagtc agttcgttgg cnnnagcatc cac 33

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Tyr Ala Ser Glu Ser Met Ser
1 5

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
tatgcttctg agtctatgtc t 21

<210> SEQ ID NO 21
<211> LENGTH: 7
<212> TYPE: PRT
<213> ORGANISM: Artificial Sequence -continued
<220> FEATURE:
<223> OTHER INFORMATION: Synthetic

<400> SEQUENCE: 21

Tyr Ala Ser Glu Tyr Met Ser
1               5

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
tatgcttctg agtatatgtc t 21

<210> SEQ ID NO 23
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 23

Tyr Ala Ser Glu Xaa Met Ser
1               5

<210> SEQ ID NO 24
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(15)
<223> OTHER INFORMATION: n is a, c, g, or t

<400> SEQUENCE: 24
tatgcttctg agnnnatgtc t 21

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Tyr Ala Ser Glu Ser Arg Ser
1               5

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
tatgcttctg agtctaggtc t 21

-continued

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Tyr Ala Ser Glu Ser Lys Ser
1 5

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
tatgcttctg agtctaagtc t 21

<210> SEQ ID NO 29
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 29

Tyr Ala Ser Glu Ser Xaa Ser
1 5

<210> SEQ ID NO 30
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(18)
<223> OTHER INFORMATION: n is a, c, g, or t

<400> SEQUENCE: 30
tatgcttctg agtctnnntc t 21

<210> SEQ ID NO 31
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa can be any naturally occurring amino acid

<400> SEQUENCE: 31

Tyr Ala Ser Glu Xaa Xaa Ser
1 5

<210> SEQ ID NO 32
<211> LENGTH: 21
<212> TYPE: DNA
<213> ORGANISM: Artificial Sequence -continued
<220> FEATURE:
<223> OTHER INFORMATION: Synthetic
<220> FEATURE:
<221> NAME/KEY: misc_feature
<222> LOCATION: (13)..(18)
<223> OTHER INFORMATION: n is a, c, g, or t

<400> SEQUENCE: 32
tatgcttctg agnnnnnntc t 21

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gln Gln Ser His Ser Trp His Phe Thr
1 5

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
caacaaagtc atagctggca tttcacg 27

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Gly Phe Thr Phe Ser Asn His Trp Met Asn
1 5 10

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
ggattcactt tcagtaacca ctggatgaac 30

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Gly Phe Lys Phe Ser Asn His Trp Met Asn
1 5 10

<210> SEQ ID NO 38
<211> LENGTH: 30
<212> TYPE: DNA
<213> ORGANISM: Artificial Sequence -continued
<220> FEATURE:
<223> OTHER INFORMATION: Synthetic

<400> SEQUENCE: 38
ggattcaagt tcagtaacca ctggatgaac 30

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Gly Phe Pro Phe Ser Asn His Trp Met Asn
1 5 10

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40
ggattccctt tcagtaacca ctggatgaac 30

<210> SEQ ID NO 41
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 41

Gly Phe Xaa Phe Ser Asn His Trp Met Asn
1 5 10

<210> SEQ ID NO 42
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 42
ggattcnnnt tcagtaacca ctggatgaac 30

<210> SEQ ID NO 43
<211> LENGTH: 19
<212> TYPE: PRT
<213> ORGANISM: Artificial Sequence
<220> FEATURE:
<223> OTHER INFORMATION: Synthetic

<400> SEQUENCE: 43

Glu Ile Arg Ser Lys Ser Ile Asn Ser Ala Thr His Tyr Ala Glu Ser
1 5 10 15

Val Lys Gly

-continued

<210> SEQ ID NO 44
<211> LENGTH: 57
<212> TYPE: DNA
<213> ORGANISM: Artificial Sequence
<220> FEATURE:
<223> OTHER INFORMATION: Synthetic

<400> SEQUENCE: 44
gaaattagat caaaatctat taattctgca acacattatg cggagtctgt gaaaggg 57

<210> SEQ ID NO 45
<211> LENGTH: 19
<212> TYPE: PRT
<213> ORGANISM: Artificial Sequence
<220> FEATURE:
<223> OTHER INFORMATION: Synthetic

<400> SEQUENCE: 45

Glu Ile Arg Ser Lys Ser Met Asn Ser Ala Thr His Tyr Ala Glu Ser
1 5 10 15

Val Lys Gly

<210> SEQ ID NO 46
<211> LENGTH: 57
<212> TYPE: DNA
<213> ORGANISM: Artificial Sequence
<220> FEATURE:
<223> OTHER INFORMATION: Synthetic

<400> SEQUENCE: 46
gaaattagat caaaatctat gaattctgca acacattatg cggagtctgt gaaaggg 57

<210> SEQ ID NO 47
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 47

Glu Ile Arg Ser Lys Ser Xaa Asn Ser Ala Thr His Tyr Ala Glu Ser
1 5 10 15

Val Lys Gly

<210> SEQ ID NO 48
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(21)
<223> OTHER INFORMATION: n is a, c, g, or t

<400> SEQUENCE: 48
gaaattagat caaaatctnn naattctgca acacattatg cggagtctgt gaaaggg 57

<210> SEQ ID NO 49
<211> LENGTH: 19
<212> TYPE: PRT

<213> ORGANISM: Artificial Sequence
<220> FEATURE:
<223> OTHER INFORMATION: Synthetic

<400> SEQUENCE: 49

Glu Ile Arg Ser Lys Ser Ile Asn Ser Ala Thr His Tyr Ala Arg Ser
1 5 10 15

Val Lys Gly

<210> SEQ ID NO 50
<211> LENGTH: 57
<212> TYPE: DNA
<213> ORGANISM: Artificial Sequence
<220> FEATURE:
<223> OTHER INFORMATION: Synthetic

<400> SEQUENCE: 50
gaaattagat caaaatctat taattctgca acacattatg cgcgttctgt gaaaggg 57

<210> SEQ ID NO 51
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 51

Glu Ile Arg Ser Lys Ser Ile Asn Ser Ala Thr His Tyr Ala Xaa Ser
1 5 10 15

Val Lys Gly

<210> SEQ ID NO 52
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (43)..(45)
<223> OTHER INFORMATION: n is a, c, g, or t

<400> SEQUENCE: 52
gaaattagat caaaatctat taattctgca acacattatg cgnnntctgt gaaaggg 57

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

Asn Tyr Tyr Gly Ser Thr Tyr Asp His
1 5

<210> SEQ ID NO 54
<211> LENGTH: 27
<212> TYPE: DNA
<213> ORGANISM: Artificial Sequence
<220> FEATURE:
<223> OTHER INFORMATION: Synthetic -continued

<400> SEQUENCE: 54
aattactacg gtagtaccta cgaccat 27

<210> SEQ ID NO 55
<211> LENGTH: 19
<212> TYPE: PRT
<213> ORGANISM: Artificial Sequence
<220> FEATURE:
<223> OTHER INFORMATION: Synthetic

<400> SEQUENCE: 55

Glu Ile Arg Ser Lys Ser Met Asn Ser Ala Thr His Tyr Ala Arg Ser
1 5 10 15

Val Lys Gly

<210> SEQ ID NO 56
<211> LENGTH: 57
<212> TYPE: DNA
<213> ORGANISM: Artificial Sequence
<220> FEATURE:
<223> OTHER INFORMATION: Synthetic

<400> SEQUENCE: 56
gaaattagat caaaatctat gaattctgca acacattatg cgcgttctgt gaaaggg 57

<210> SEQ ID NO 57
<211> LENGTH: 23
<212> TYPE: PRT
<213> ORGANISM: Homo sapiens

<400> SEQUENCE: 57

Glu Ile Val Leu Thr Gln Ser Pro Asp Phe Gln Ser Val Thr Pro Lys
1 5 10 15

Glu Lys Val Thr Ile Thr Cys
20

<210> SEQ ID NO 58
<211> LENGTH: 15
<212> TYPE: PRT
<213> ORGANISM: Homo sapiens

<400> SEQUENCE: 58

Trp Tyr Gln Gln Lys Pro Asp Gln Ser Pro Lys Leu Leu Ile Lys
1 5 10 15

<210> SEQ ID NO 59
<211> LENGTH: 32
<212> TYPE: PRT
<213> ORGANISM: Homo sapiens

<400> SEQUENCE: 59

Gly Val Pro Ser Arg Phe Ser Gly Ser Gly Ser Gly Thr Asp Phe Thr
1 5 10 15

Leu Thr Ile Asn Ser Leu Glu Ala Glu Asp Ala Ala Thr Tyr Tyr Cys
20 25 30

<210> SEQ ID NO 60
<211> LENGTH: 10
<212> TYPE: PRT
<213> ORGANISM: Homo sapiens

<400> SEQUENCE: 60

Phe Gly Gln Gly Thr Lys Val Glu Ile Lys

-continued 1 5 10

<210> SEQ ID NO 61
<211> LENGTH: 69
<212> TYPE: DNA
<213> ORGANISM: Homo sapiens

<400> SEQUENCE: 61
gaaattgtgc tgactcagtc tccagacttt cagtctgtga ctccaaaaga gaaagtcacc 60
atcacctgc 69

<210> SEQ ID NO 62
<211> LENGTH: 45
<212> TYPE: DNA
<213> ORGANISM: Homo sapiens

<400> SEQUENCE: 62
tggtaccagc agaagccaga tcagtctcca aagctcctca tcaag 45

<210> SEQ ID NO 63
<211> LENGTH: 96
<212> TYPE: DNA
<213> ORGANISM: Homo sapiens

<400> SEQUENCE: 63
ggggtcccct cgaggttcag tggcagtgga tctgggacag atttcaccct caccatcaat 60
agcctggaag ctgaagatgc tgccacgtat tactgt 96

<210> SEQ ID NO 64
<211> LENGTH: 30
<212> TYPE: DNA
<213> ORGANISM: Homo sapiens

<400> SEQUENCE: 64
ttcggccaag ggaccaaggt ggaaatcaaa 30

<210> SEQ ID NO 65
<211> LENGTH: 25
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 66
<211> LENGTH: 14
<212> TYPE: PRT
<213> ORGANISM: Homo sapiens

<400> SEQUENCE: 66

Trp Val Arg Gln Ala Pro Gly Lys Gly Leu Glu Trp Val Gly
1 5 10

<210> SEQ ID NO 67
<211> LENGTH: 32
<212> TYPE: PRT
<213> ORGANISM: Homo sapiens

<400> SEQUENCE: 67

-continued

Arg Phe Thr Ile Ser Arg Asp Asp Ser Lys Asn Ser Leu Tyr Leu Gln
1 5 10 15

Met Asn Ser Leu Lys Thr Glu Asp Thr Ala Val Tyr Tyr Cys Ala Arg
20 25 30

<210> SEQ ID NO 68
<211> LENGTH: 11
<212> TYPE: PRT
<213> ORGANISM: Homo sapiens

<400> SEQUENCE: 68

Trp Gly Gln Gly Thr Leu Val Thr Val Ser Ser
1 5 10

<210> SEQ ID NO 69
<211> LENGTH: 75
<212> TYPE: DNA
<213> ORGANISM: Homo sapiens

<400> SEQUENCE: 69
gaggtgcagc tggtggagtc tgggggaggc ttggtccagc ctggagggtc cctgagactc 60
tcctgtgcag cctct 75

<210> SEQ ID NO 70
<211> LENGTH: 42
<212> TYPE: DNA
<213> ORGANISM: Homo sapiens

<400> SEQUENCE: 70
tgggtccgcc aggctccagg gaaggggctg gagtgggttg gc 42

<210> SEQ ID NO 71
<211> LENGTH: 96
<212> TYPE: DNA
<213> ORGANISM: Homo sapiens

<400> SEQUENCE: 71
agattcacca tctcaagaga tgattcaaag aactcactgt acctgcagat gaacagcctg 60
aaaaccgagg acacggccgt gtattactgt gctaga 96

<210> SEQ ID NO 72
<211> LENGTH: 33
<212> TYPE: DNA
<213> ORGANISM: Homo sapiens

<400> SEQUENCE: 72
tggggccaag ggaccctggt caccgtctcc tca 33

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Arg Ala Pro Gln Phe Val Gly Ser Ser Ile His
1 5 10

<210> SEQ ID NO 74
<211> LENGTH: 33
<212> TYPE: DNA
<213> ORGANISM: Artificial Sequence -continued
<220> FEATURE:
<223> OTHER INFORMATION: Synthetic

<400> SEQUENCE: 74
agggcccctc agttcgttgg ctcaagcatc cac 33

<210> SEQ ID NO 75
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 75

Arg Ala Xaa Gln Phe Val Gly Ser Ser Ile His
1 5 10

<210> SEQ ID NO 76
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 76
agggccnnnc agttcgttgg ctcaagcatc cac 33

<210> SEQ ID NO 77
<211> LENGTH: 11
<212> TYPE: PRT
<213> ORGANISM: Artificial Sequence
<220> FEATURE:
<223> OTHER INFORMATION: Synthetic

<400> SEQUENCE: 77

Arg Ala Ser Gln Phe Val Tyr Ser Ser Ile His
1 5 10

<210> SEQ ID NO 78
<211> LENGTH: 33
<212> TYPE: DNA
<213> ORGANISM: Artificial Sequence
<220> FEATURE:
<223> OTHER INFORMATION: Synthetic

<400> SEQUENCE: 78
agggccagtc agttcgttta ttcaagcatc cac 33

<210> SEQ ID NO 79
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 79

-continued

Arg Ala Ser Gln Phe Val Xaa Ser Ser Ile His
1 5 10

<210> SEQ ID NO 80
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(21)
<223> OTHER INFORMATION: n is a, c, g, or t

<400> SEQUENCE: 80
agggccagtc agttcgttnn ntcaagcatc cac 33

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Gln Gln Ser His Trp Trp His Phe Thr
1 5

<210> SEQ ID NO 82
<211> LENGTH: 27
<212> TYPE: DNA
<213> ORGANISM: Artificial Sequence
<220> FEATURE:
<223> OTHER INFORMATION: Synthetic

<400> SEQUENCE: 82
caacaaagtc attggtggca tttcacg 27

<210> SEQ ID NO 83
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 83

Gln Gln Ser His Xaa Trp His Phe Thr
1 5

<210> SEQ ID NO 84
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(15)
<223> OTHER INFORMATION: n is a, c, g, or t

<400> SEQUENCE: 84
caacaaagtc atnnntggca tttcacg 27

<210> SEQ ID NO 85

-continued

<211> LENGTH: 357
<212> TYPE: DNA
<213> ORGANISM: Homo sapiens

<400> SEQUENCE: 85

```
tcagcctcca ccaagggccc atcggtcttc cccctggcac cctcctccaa gagcacctct     60
gggggcacag cggccctggg ctgcctggtc aaggactact tccccgaacc ggtgacggtg    120
tcgtggaact caggcgccct gaccagcggc gtgcacacct tcccggctgt cctacagtcc    180
tcaggactct actccctcag cagcgtggtg accgtgccct ccagcagctt gggcacccag    240
acctacatct gcaacgtgaa tcacaagccc agcaacacca aggtggacaa gaaagcagag    300
cccaaatctt ctactagtgt tctctaccca tatgatgtac ctgattatgc atcatag       357
```

<210> SEQ ID NO 86
<211> LENGTH: 324
<212> TYPE: DNA
<213> ORGANISM: Homo sapiens

<400> SEQUENCE: 86

```
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtc ttag                                           324
```

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87

```
tggctcccag gtgccaaatg tgaaattgtg ctgactcag                           39
```

<210> SEQ ID NO 88
<211> LENGTH: 21
<212> TYPE: DNA
<213> ORGANISM: Artificial Sequence
<220> FEATURE:
<223> OTHER INFORMATION: Synthetic

<400> SEQUENCE: 88

```
tggctcccag gtgccaaatg t                                               21
```

<210> SEQ ID NO 89
<211> LENGTH: 21
<212> TYPE: DNA
<213> ORGANISM: Artificial Sequence
<220> FEATURE:
<223> OTHER INFORMATION: Synthetic

<400> SEQUENCE: 89

```
gacagatggt gcagccacag t                                               21
```

<210> SEQ ID NO 90
<211> LENGTH: 39
<212> TYPE: DNA
<213> ORGANISM: Artificial Sequence
<220> FEATURE:
<223> OTHER INFORMATION: Synthetic

<400> SEQUENCE: 90

```
ctctccacag gtgtccactc ccaggtccaa ctgcaggtc                            39
```

<210> SEQ ID NO 91
<211> LENGTH: 21

-continued

```
<212> TYPE: DNA
<213> ORGANISM: Artificial Sequence
<220> FEATURE:
<223> OTHER INFORMATION: Synthetic

<400> SEQUENCE: 91

ctctccacag gtgtccactc c                                              21


<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92

gaagaccgat gggcccttgg t                                              21
```